United States Patent
Baba

(10) Patent No.: US 9,526,467 B2
(45) Date of Patent: Dec. 27, 2016

(54) RADIATION IMAGE PICK-UP DEVICE AND IMAGE PROCESSING METHOD

(71) Applicant: Hitachi Medical Corporation, Tokyo (JP)

(72) Inventor: Rika Baba, Tokyo (JP)

(73) Assignee: HITACHI, LTD., Tokyo (JP)

(*) Notice: Subject to any disclaimer, the term of this patent is extended or adjusted under 35 U.S.C. 154(b) by 302 days.

(21) Appl. No.: 14/383,291

(22) PCT Filed: Jan. 25, 2013

(86) PCT No.: PCT/JP2013/051645
§ 371 (c)(1),
(2) Date: Sep. 5, 2014

(87) PCT Pub. No.: WO2013/145831
PCT Pub. Date: Oct. 3, 2013

(65) Prior Publication Data
US 2015/0036788 A1 Feb. 5, 2015

(30) Foreign Application Priority Data
Mar. 27, 2012 (JP) .................................. 2012-071918

(51) Int. Cl.
*G06K 9/00* (2006.01)
*A61B 6/00* (2006.01)
(Continued)

(52) U.S. Cl.
CPC ............. *A61B 6/5211* (2013.01); *A61B 6/027* (2013.01); *A61B 6/032* (2013.01); *A61B 6/4441* (2013.01);
(Continued)

(58) Field of Classification Search
None
See application file for complete search history.

(56) References Cited

U.S. PATENT DOCUMENTS

| 6,236,704 B1 | 5/2001 | Navab et al. |
| 7,778,392 B1* | 8/2010 | Berman ............... A61B 6/032 378/210 |

(Continued)

FOREIGN PATENT DOCUMENTS

| JP | 9-327453 A | 12/1997 |
| JP | 2001-29342 A | 2/2001 |

(Continued)

OTHER PUBLICATIONS

Tetsuo Imanishi, Evaluation of Tomosynthesis Using Sonialvision safire Digital Table, Medical Now No. 62, Jul. 2007.
(Continued)

*Primary Examiner* — Soo Park
(74) *Attorney, Agent, or Firm* — Baker Botts L.L.P.

(57) ABSTRACT

Irrespective of the layout, moving path, and moving range of the X-ray source and the detector, a highly precise image is acquired, in a similar manner as an X-ray CT scanner that is capable of acquiring a measured image using a rotation angle of 180 degrees or more. A measured image detected by the detector is converted into a rotationally measured image that is acquired by rotationally moving the X-ray source and the detector along concentric circular paths. Then, the rotationally measured image at every measurement angle is provided with a weight that gives intensity variation equivalent to that of the reconstructed image obtained from the rotationally measured images acquired by the measurement using the rotation angle range of 180 degrees, a reconstruction operation is performed, and a reconstructed image is obtained.

14 Claims, 14 Drawing Sheets

(51) Int. Cl.
  *G06T 11/00* (2006.01)
  *A61B 6/02* (2006.01)
  *A61B 6/03* (2006.01)
  *A61B 6/14* (2006.01)

(52) U.S. Cl.
  CPC .......... *A61B 6/5205* (2013.01); *G06T 11/005* (2013.01); *G06T 11/006* (2013.01); *A61B 6/14* (2013.01); *A61B 6/50* (2013.01); *A61B 6/5258* (2013.01); *G06T 2207/10081* (2013.01); *G06T 2207/10116* (2013.01); *G06T 2211/40* (2013.01)

(56) References Cited

U.S. PATENT DOCUMENTS 8,824,765 B2 * 9/2014 Dennerlein .......... G06T 11/006
  382/131
8,923,589 B2 * 12/2014 Noda .................. G06T 11/006
  382/131
9,001,963 B2 * 4/2015 Sowards-Emmerd G06T 11/006
  378/11
9,420,975 B2 * 8/2016 Gutfleisch ............. A61B 6/025
2002/0154728 A1 10/2002 Morita et al.

FOREIGN PATENT DOCUMENTS

JP   2002-263093 A   9/2002
JP   2012-10891 A   1/2012

OTHER PUBLICATIONS

International Preliminary Report for PCT/JP2013/051645, dated Oct. 9, 2014.

* cited by examiner

RADIATION IMAGE PICK-UP DEVICE AND IMAGE PROCESSING METHOD

TECHNICAL FIELD

The present invention relates to a radiation imaging technique, and in particular, it relates to a technique for reconstructing a desired tomographic image, from measured images obtained by imaging a subject from a plurality of different directions.

BACKGROUND ART

There is an X-ray CT scanner in which an X-ray source and a two-dimensional X-ray detector are installed in such a manner that they are opposed to each other, and X-ray imaging is performed while a pair of the X-ray source and the detector rotates around the subject. In the X-ray CT scanner, a series of measured images acquired through the detector are subjected to an arithmetic processing for reconstruction, whereby a reconstructed image is obtained, resulting in a desired cross-sectional image. The X-ray CT scanner needs measured images that are acquired by rotating the X-ray source by 180 degrees or more, in order to obtain a reconstructed image with a high degree of precision. Therefore, it is necessary to establish a large-scale apparatus.

In comparison to the X-ray CT scanner, there are small-sized devices, such as an X-ray imaging apparatus in which the X-ray source and the detector are allowed to perform rotational transfer within only a range much narrower than 180 degrees as a rotation angle, and another X-ray imaging apparatus in which the movement of the X-ray source and the detector is not the rotational transfer. As a representative example, there is a tomographic apparatus that linearly moves the X-ray source and the detector respectively in the directions opposite to each other, so as to perform tomosynthesis imaging (e.g., see the Non Patent Document 1). The tomosynthesis imaging employs a so-called summation method that applies a summation process to the measured images obtained by the detector, so as to acquire an image.

PRIOR ART DOCUMENT

Non Patent Document

Non Patent Document 1
Tetsuo Imanishi "Evaluation of Tomosynthesis Using SONIALVISION safire Digital Table", [online], Shimazu Technical Library [searched on Mar. 27, 2012], the Internet <URL: http://www.shimadzu.com.tr/p.aspx?deger=medical/oh80jt0000001xar.h tml>

DISCLOSURE OF THE INVENTION

Problem to be Solved by the Invention

However, in the reconstruction method of the conventional X-ray CT scanner, if the image is reconstructed from the measured images obtained by using the rotation angle less than 180 degrees, a high-quality image is hardly obtained. This happens similarly for the quality of image obtained by the summation method in the tomosynthesis imaging. In addition, since an image obtained by the summation method is different in dimension from the image obtained by the reconstruction method of the X-ray CT scanner, comparison is difficult between the image obtained by the summation method and the image obtained by the reconstruction method of the X-ray CT scanner.

The present invention has been made in view of the situation above, and an object of the present invention is to provide a technique for acquiring an image with a high degree of precision, in a manner similar to the X-ray CT scanner that is capable of acquiring measured images by using the rotation angle of 180 degrees of more, irrespective of the layout, moving path, and moving range of the X-ray source and the detector.

Means to Solve the Problem

The present invention converts a measured image detected by the detector into a rotationally measured image that is obtained by moving the X-ray source and the detector rotationally along concentric circular paths around the subject assumed as a center, and a weight is applied in response to each measurement angle of the rotationally measured image, so that a reconstructed image obtained from the rotationally measured image indicates variation of intensity, being equivalent to the reconstructed image obtained by the measurement with a rotation angle range being 180 degrees.

Specifically, a radiation imaging apparatus being provided with an X-ray source configured to irradiate a subject with X-rays, a detector configured to detect the X-rays, a measuring processor configured to relatively move the X-ray source and the detector so as to obtain a measured image, and an image processor configured to apply an arithmetic processing to the measured image so as to obtain an image, the image processor including, a converter to convert the measured image into a rotationally measured image acquired within a predetermined rotation angle range when the X-ray source and the detector move rotationally along concentric circular paths, and a reconstructor configured to apply a weight responsive to a measurement angle to the rotationally measured image, perform a reconstruction operation, and obtain a reconstructed image, wherein the predetermined rotation angle range for acquiring the rotationally measured image includes at least one unit rotation angle range for sequentially acquiring the rotationally measured images, the unit rotation angle range is less than 180 degrees, and the weight provides the reconstructed image obtained from the rotationally measured images, with intensity variation equivalent to the intensity variation of the reconstructed image obtained from the measurement using the rotation angle range of 180 degrees.

Effect of the Invention

According to the present invention, it is possible acquire an image with a high degree of precision, in a manner similar to an X-ray CT scanner that is capable of acquiring a measured image by using the rotation angle of 180 degrees of more, irrespective of the layout, moving path, and moving range of the X-ray source and the detector.

BEST MODE FOR CARRYING OUT THE INVENTION

First Embodiment

Hereinafter, the first embodiment to which the present invention is applied will be explained with reference to the accompanying drawings. In the entire drawings for explaining the embodiments of the present invention, constituents named and labeled the same, and having the same function shall not be tediously explained.

Figure 1A:
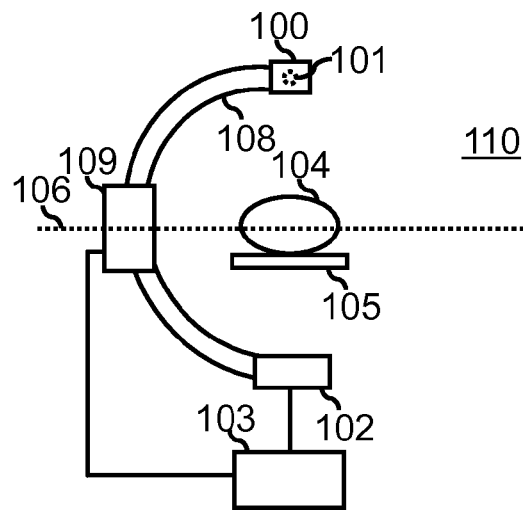
FIG. 1A, FIG. 1B, and FIG. 1C show an overview of the X-ray imaging apparatus according to the first embodiment.
Figure 1B:
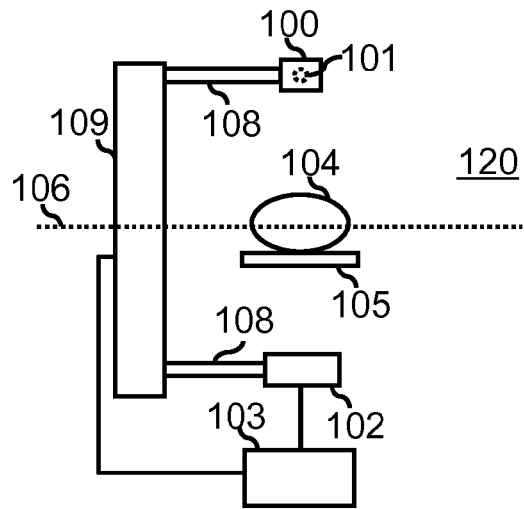
Figure 1C:
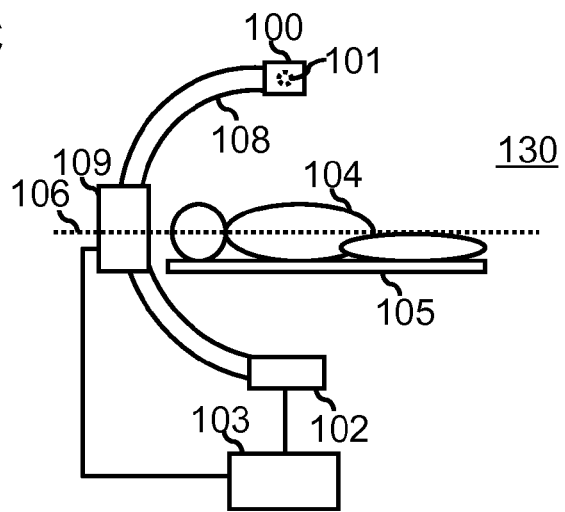

FIG. 1A, FIG. 1B, and FIG. 1C are each showing an overview of the X-ray imaging apparatus 110, 120, and 130 relating to the present embodiment. The X-ray imaging apparatus 110, 120, and 130 of present embodiment is provided with the X-ray tube 100 having the X-ray source 101 to irradiate the subject 104 with X-rays, the detector 102 for detecting the X-rays, the controller 103, the arm 108, and the shifter 109. The reference numeral 105 in the figure indicates a bed for placing the subject 104 thereon. The X-ray source 101 within the X-ray tube 100 and the detector 102 are connected to the shifter 109 via the arm 108. The controller 103 sends a directive to the shifter 109 to move the X-ray source 101 and the detector 102.

In the X-ray imaging apparatus 110 and 130 as shown in FIG. 1A and FIG. 1C, the arm 108 is in C-shape, and the X-ray source 101 and the detector 102 move rotationally along the circular paths around the rotation axis 106 on the paper surface. It is to be noted that in the X-ray imaging apparatus 110 and 130 shown in FIG. 1A and FIG. 1C, the shape of the arm is not limited to the C-shape. It may be a U-shape, or a squared U-shape.

In the X-ray imaging apparatus 120 as shown in FIG. 1B, the X-ray source 101 and the detector 102 are mounted on different arms 108, respectively. In the X-ray imaging apparatus 120, the X-ray source 101 and the detector 102 perform parallel movement, rotational movement, and both rotational and parallel movement. By way of example, the X-ray source 101 and the detector 102 move in parallel with the bed 105 or the floor surface in the direction perpendicular to the paper surface. Alternatively, they move along the circular path about the rotation axis 106 on the paper surface.

Further alternatively, the X-ray source 101 moves in parallel with the bed 105 or the floor surface in the direction perpendicular to the paper surface, and the detector 102 moves along the circular paths about the rotation axis 106 on the paper surface. Further alternatively, the X-ray source 101 moves along the circular path about the rotation axis 106 on the paper surface, and the detector 102 moves in parallel with the bed 105 or the floor surface in the direction perpendicular to the paper surface.

In the X-ray imaging apparatus 110 and 120 as shown in FIG. 1A and FIG. 1B, the subject 104 is placed in such a manner that his or her body axis is orthogonal to the rotation axis 106. Therefore, the rotatable angle range is narrower than 180 degrees. On the other hand, in the X-ray imaging apparatus 130 as shown in FIG. 1C, the subject 104 is placed in such a manner that his or her body axis is parallel to the rotation axis 106. Therefore, the rotatable angle range becomes wider, and the image quality of a cross-sectional image may be enhanced. Moreover, this allows the X-ray source 101 and the detector 102 to rotate around the side surface of the subject 104, enabling acquisition of a measured image viewed from the side surface of the subject 104, and thus it is possible to obtain a favorable cross-sectional image viewed from the side direction.

It is to be noted here that various positional relationships are conceivable between the body axis of the subject 104 and the rotation axis 106. The distance between the bed 105 and the X-ray source 101, and the distance between the bed and the detector 102 may be set shorter, compared to the distance as shown in FIG. 1A to FIG. 1C. It is also possible to configure such that the X-ray source 101 and the detector 102 move along the circular paths different from each other. Furthermore, the external shape of the X-ray imaging apparatus may not be limited to those illustrated in FIG. 1A to FIG. 1C. The X-ray source 101 and the detector 102 may move along any path, other than the rotational movement and the parallel movement.

X-rays generated from the X-ray source 101 pass through the subject 104, the detector 102 converts the X-rays into electrical signals responsive to intensity of the X-rays, and the electrical signals are inputted into the controller 103 as measured data (measured image). The controller 103 converts the measured image being inputted into a three-dimensional reconstructed image. The controller 103 controls, in addition to reconstructing an image, generation of X-rays in the X-ray source 101, acquisition of the measured image by the detector 102, and movement of the X-ray source 101 and the detector 102. It is to be noted that hereinafter in the present specification, data prior to the image processing is referred to as a "measured image", including data generally called as a projected image obtained by subjecting the measured image acquired by the detector 102 to sensitivity correction, and the like.

The detector 102 employs a two-dimensional detector. In the present embodiment, an array obtained by arranging one-dimensional detectors in plural lines is also regarded as the two-dimensional detector. A flat X-ray detector, a combination of an X-ray image intensifier and a CCD camera, an imaging plate, a CCD detector, a solid-state detector, and the like, may be considered as the two-dimensional detector. The flat X-ray detector may include the following; a pair of amorphous silicon photo diode and TFT is established, pairs thereof being arranged on a square matrix, and those are directly combined with a fluorescent plate, and the like. It is further possible to employ a film as the detector, and this film is read by a film digitizer to obtain the measured image.

Hereinafter, an explanation will be provided, taking as an example that the present embodiment employs the X-ray imaging apparatus 120 as illustrated in FIG. 1B and tomosynthesis imaging is performed. Generally, in the tomosynthesis imaging, the X-ray source 101 and the detector 102 are moved synchronously in the directions opposite to each other, in parallel to the bed 105. Then, measured images detected respectively at the positions of the detector 102 are summed up, and an image is obtained. This method is referred to as a summation method.

Figure 2A:
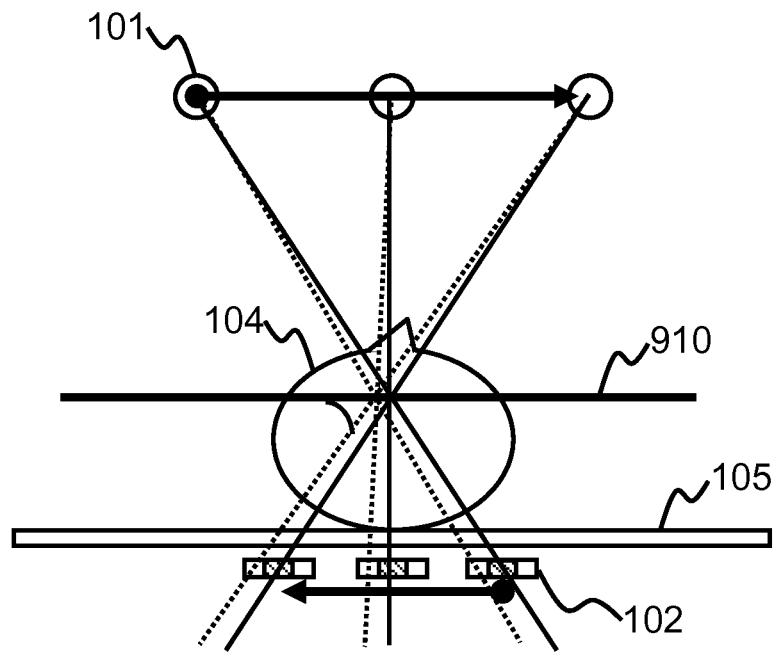
FIG. 2A and FIG. 2B are illustrations for explaining a principle of the tomosynthesis imaging.
Figure 2B:
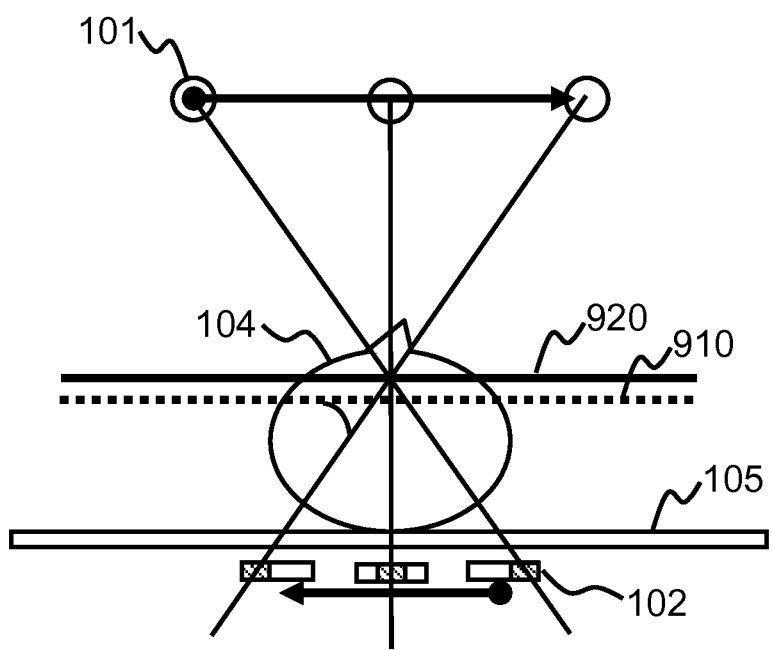

FIG. 2A and FIG. 2B illustrate the principle of the summation method of the tomosynthesis imaging. As illustrated in FIG. 2A, when the X-ray source 101 moves in the direction opposite to the direction of the detector 102, focus is achieved only on one plane 910 being parallel to the moving direction, and not on other planes. When the measured images are summed up, structures on the planes where focus is not achieved become blurred and invisible, and only the structure existing on the plane being focused is enhanced, thereby obtaining a cross-sectional image on the focused position.

It is to be noted that in the tomosynthesis imaging, variation of moving velocity of the X-ray source 101 and the detector 102 allows the position of the focused plane 910 to be variable. If a flat-panel detector is employed as the detector 102, an element position in the detector 102 is shifted when performing the summation, instead of varying the moving velocity, thereby varying the focused plane 910 to any position.

By way of example, as shown in FIG. 2A, it is assumed to use the flat-panel detector having three detection elements in the moving direction. The X-ray beam directed to the central detection element is indicated by a solid line, and the X-ray beam directed to the left-end detection element is indicated by a dotted line. Each of those X-ray beams come into focus on the plane 910 indicated also by a solid line. When the measured images being obtained are summed up, a cross-sectional image of the plane 910 is obtained.

It is to be noted that as shown in FIG. 2B, there is another method referred to as a shift-and-add method that shifts the element position at the time of summation. In the shift-and-add method, a value of the left-end element is added in the measured image being detected when the detector 102 is positioned on the left side, a value of the central element is added in the measured image being detected when the detector 102 is positioned at the center, a value of the right-end element is added in the measured image being detected when the detector 102 is positioned on the right side. The X-ray beams directed to the respective elements targeted for the summation achieve focus on the plane 920 indicated by the solid line. As described above, by shifting the element position when summation is performed, it is possible to obtain a cross-sectional image at a position different from the plane 910 where focus is achieved by the summation method shown in FIG. 2A.

Next, an explanation will be provided regarding a principle of the reconstruction process in the CT imaging in which the X-ray source 101 and the detector 102 rotationally move along concentric circular paths. Here, a filtered back-projection method will be taken as an example for making the explanation. In the CT imaging, the X-ray source 101 and the detector 102 are rotated, and the measured image is obtained at every predetermined angle (measurement angle). From those measured images obtained at the respective measurement angles, a reconstructed image is obtained according to the filtered back-projection method. The filtered back-projection method is a method that applies a reconstruction filter to the measured images obtained at every measurement angle, and then performs the summation process, so as to obtain the reconstructed image. According to the filtered back-projection method, values of the elements which the X-ray beams enter are summed up, the X-ray beams passing through an arbitrary pixel of the reconstructed image. Then, focus is achieved on a structure projected on the measured images at all the angles and therefore the structure is highlighted. On the other hand, a structure projected on the measured images at only partial angles do not achieve focus, and this structure becomes blurred and invisible. In the CT imaging, in order to perform accurate reconstruction processing, it is necessary that the X-ray source 101 and the detector 102 are rotated by 180 degrees or more, and with the use of thus obtained measured images a reconstruction operation is performed.

Figure 3:
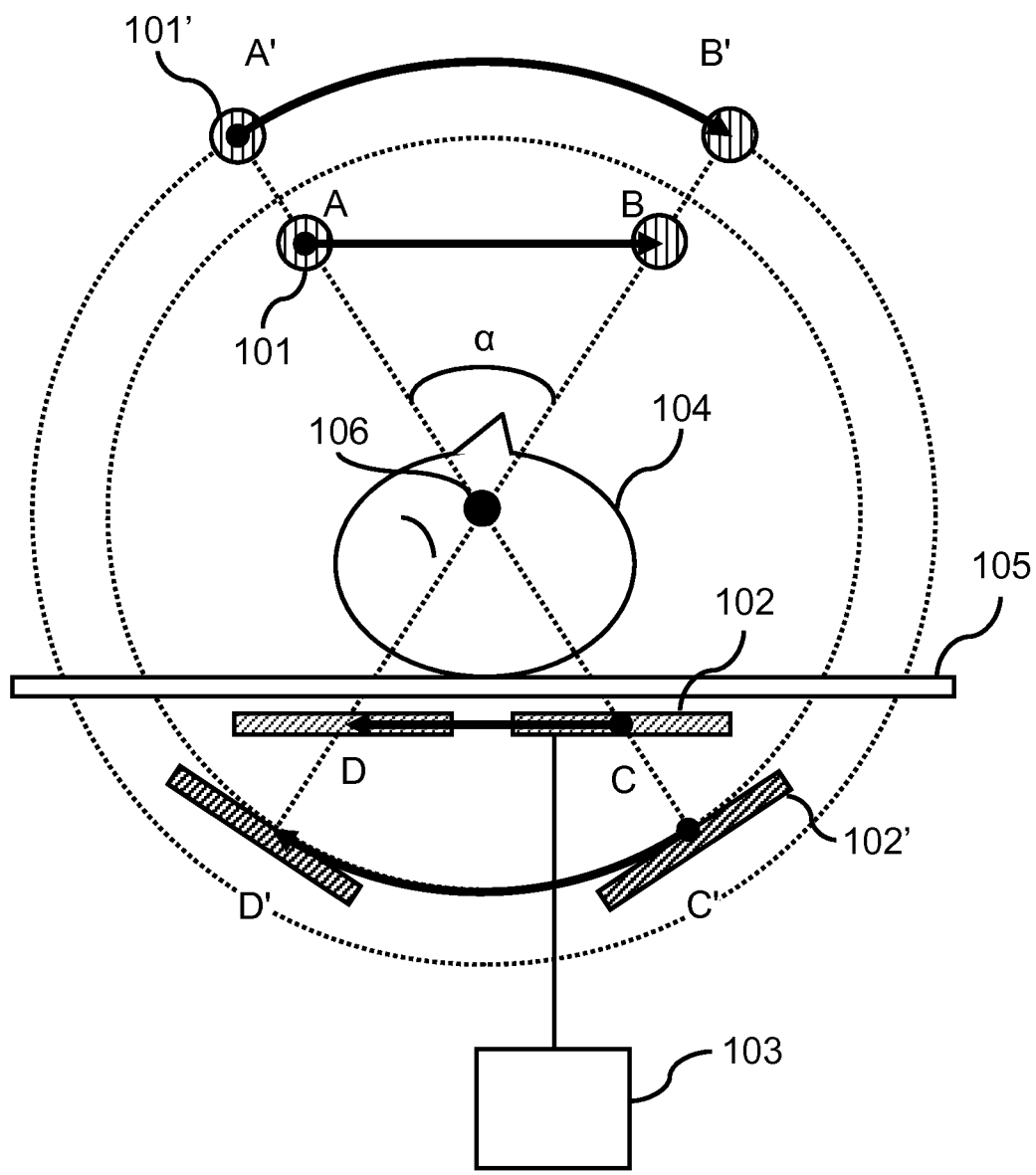
FIG. 3 schematically illustrates the processing of the first embodiment.

As shown in FIG. 3, in the present embodiment, the measured images obtained by the tomosynthesis imaging are converted into rotationally measured images obtained by a device that rotationally moves the X-ray source 101 and the detector 102 along concentric circular paths, and then a reconstruction process is performed. Here, FIG. 3 schematically illustrates the process for converting the measured image of the present embodiment, and it is a cross-sectional view of the X-ray imaging apparatus 120, being orthogonal to the rotation axis 106, including the X-ray source 101 and the detector 102. As illustrated, the rotationally measured images obtained by converting the measured images obtained by the tomosynthesis imaging, are associated with the rotation angle range $\alpha$ being less than 180 degrees. Therefore, an artifact remains in the reconstructed image. In view of this, weights responsive to the measurement angles are applied on the rotationally measured images at the respective measurement angles, and structures in proximity to the edges of the rotation angle range are forced to be attenuated.

Figure 4A:
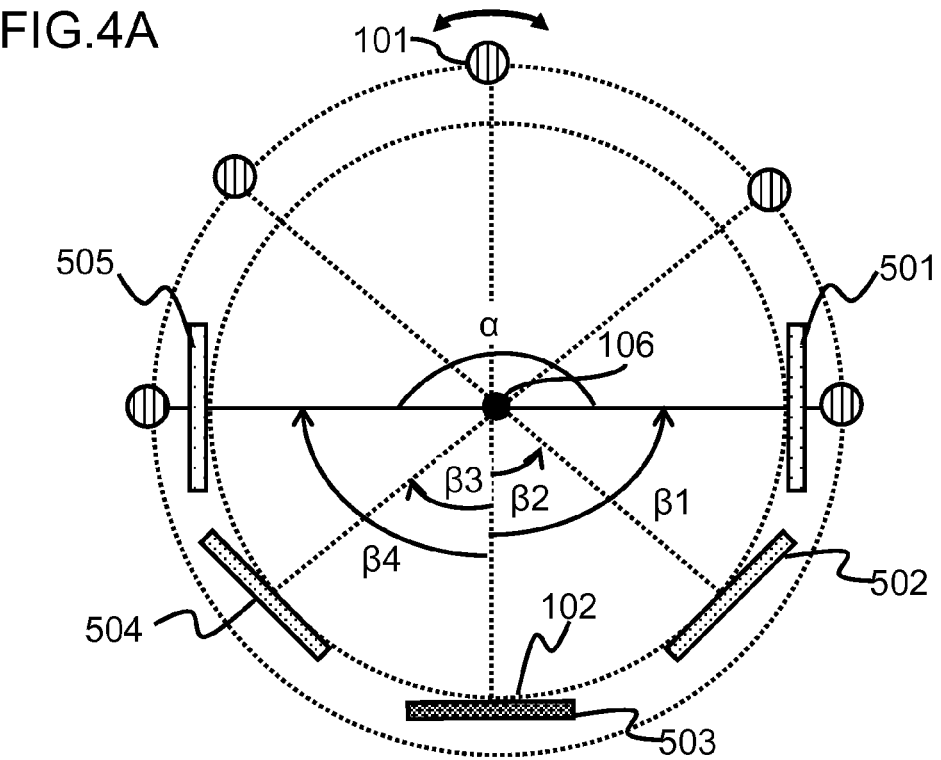
FIG. 4A illustrates the intensity of the rotationally measured images using 180 degrees.
Figure 4B:
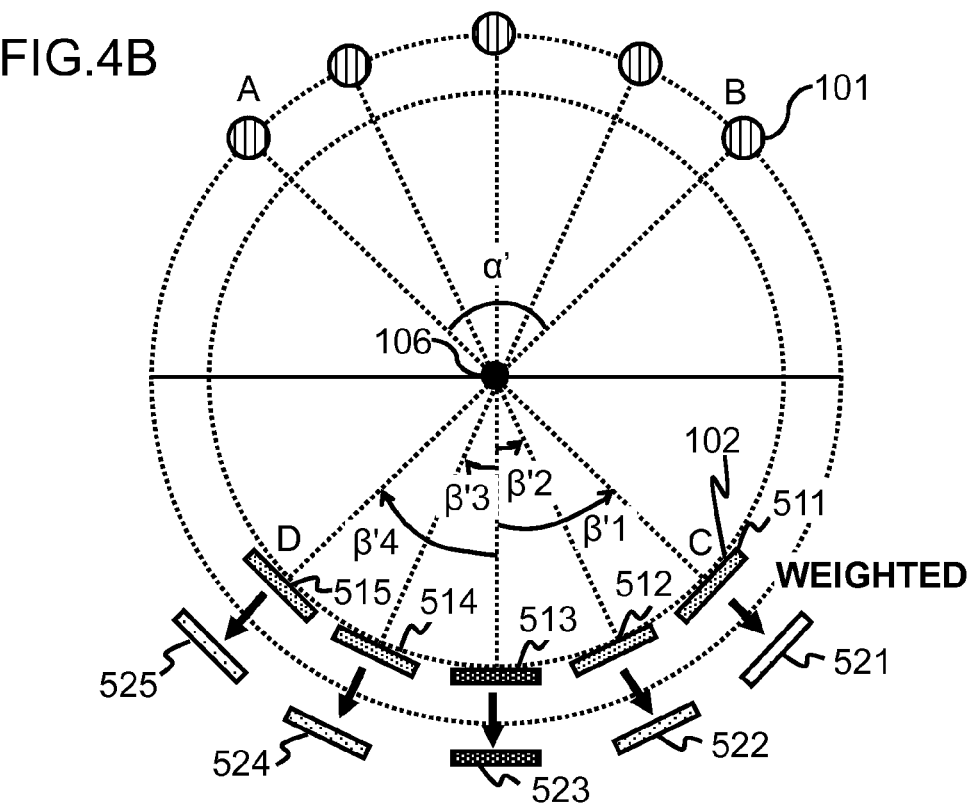
FIG. 4B illustrates the intensity and weighting of the rotationally measured images according to the first embodiment.

With reference to FIG. 4A and FIG. 4B, weighting process of the present embodiment will be explained. FIG. 4A illustrates the intensity 501, 502, 503, 504, and 505 of the rotationally measured images respectively at the measurement angles $\beta 1$, $\beta 2$, $\beta 3$, and $\beta 4$, when the rotation angle range $\alpha$ is 180 degrees. FIG. 4B illustrates the intensity 511, 512, 513, 514, and 515 of the rotationally measured images without applying any weight, respectively at the measurement angles $\beta'1$, $\beta'2$, $\beta'3$, and $\beta'4$, when the rotation angle range $\alpha$ is less than 180 degrees. In the present embodiment, weights are applied on the intensity 511, 512, 513, 514, and 515 of the rotationally measured images, thereby establishing rotationally measured images 521, 522, 523, 524, and 525 having the intensity variation equivalent to the intensity variation of the rotationally measured images when the rotation angle range $\alpha$ is 180 degrees. It is to be noted here that the measurement angle of each rotationally measured image is represented by the angle from the center of the rotation angle range $\alpha$.

Figure 5:
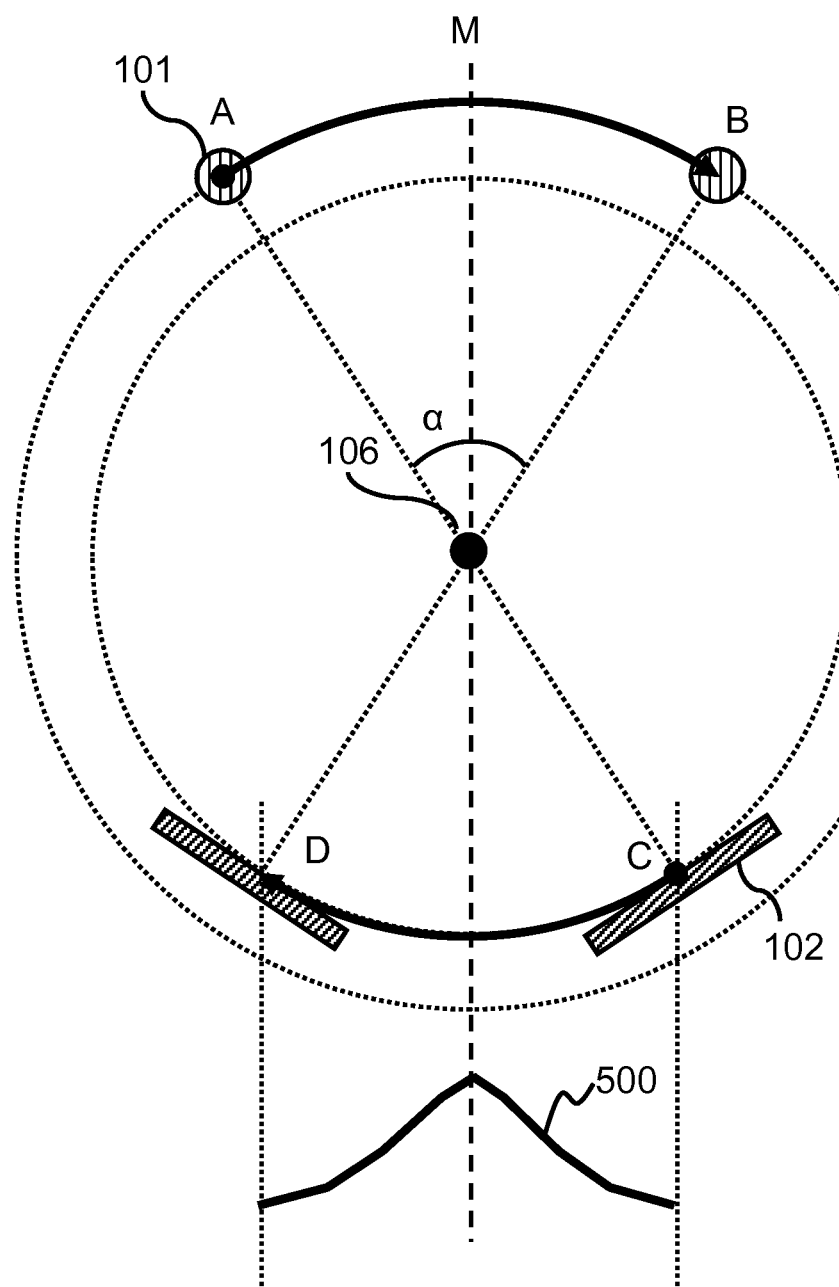
FIG. 5 illustrates a profile of the weight according to the first embodiment.

In order to implement such conversion as described above, FIG. 5 illustrates a profile of weight variation (weight variation profile) 500 to be applied to the rotationally measured images, respectively. As shown in FIG. 5, for instance, the weight variation profile is maximized at the center in the rotation angle range $\alpha$, and it becomes smaller as approaching the periphery.

Figure 6:
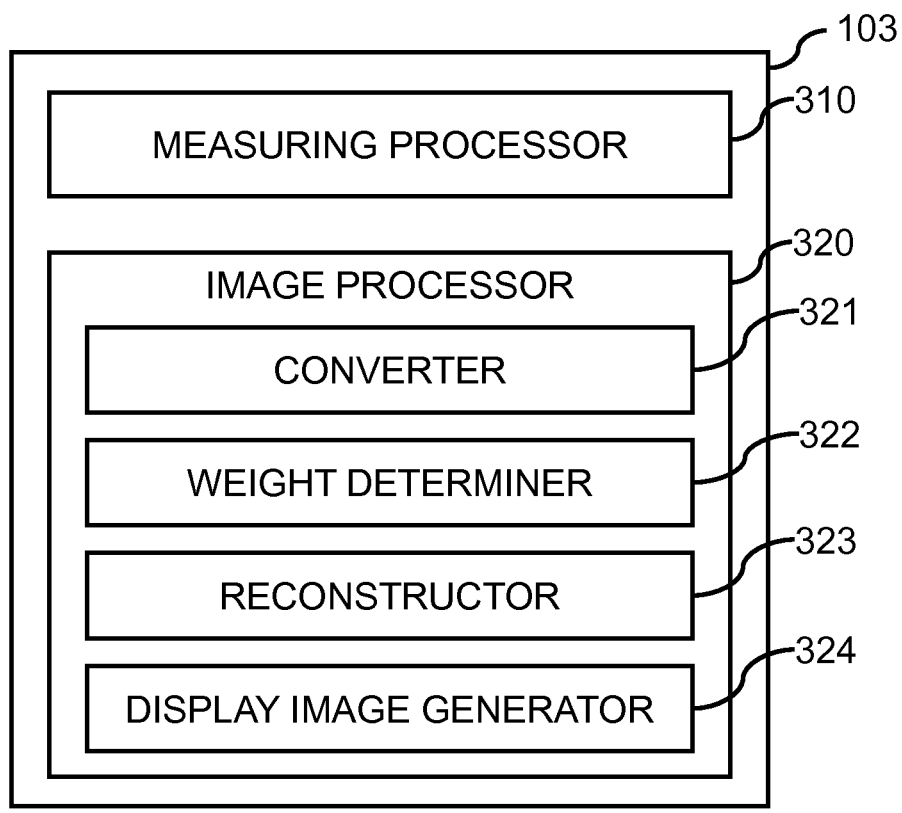
FIG. 6 is a functional block diagram of the controller according to the first embodiment.

As illustrated in FIG. 6, in order to implement the configuration above, the controller 103 of the present embodiment is provided with the measuring processor (measuring means) 310 configured to perform imaging while relatively moving the X-ray source 101 and the detector 102 so as to obtain a measured image, and an image processor (image processing means) 320 configured to apply an image processing operation to the measured image and obtain a tomographic image being a display image.

The controller 103 of the present embodiment is provided with a CPU, a memory, and a storage, and the CPU loads into the memory, programs held in the storage in advance, and executes the programs so as to implement those functions.

The measuring processor 310 of the present embodiment moves linearly the X-ray source 101 and the detector 102 synchronously in the directions opposite to each other, in the direction along the bed 105, performs the tomosynthesis imaging, and obtains the measured image. With reference to FIG. 3, the operation of the X-ray source 101 and the detector 102 of the present embodiment will be explained when the measuring processor 310 performs the tomosynthesis imaging. As illustrated, the X-ray source 101 moves from the position A to the position B. During this period, the detector 102 moves from the position C to the position D, and measured images are obtained respectively at predetermined angles, at extremely short intervals being predetermined.

The image processor 320 of the present embodiment converts the measured image obtained by the measuring processor 310 into the rotationally measured image, applies the weight responsive to each measurement angle, and obtains the reconstructed image. Then, the image processor generates a tomographic image (cross-sectional image) from thus obtained reconstructed image. In order to implement the processing above, as shown in FIG. 6, the image processor 320 of the present embodiment is provided with the converter (converting means) 321 configured to convert the measured image into the rotationally measured image obtained in a predetermined rotation angle range when the X-ray source 101 and the detector 102 rotationally move along concentric circular paths, and the reconstructor (reconstruction means) 323 configured to apply the weight responsive to each measurement angle, to the rotationally measured images, and perform a reconstruction operation to obtain a reconstructed image. In this situation here, the rotation angle range for acquiring the rotationally measured image includes at least one unit rotation angle range for sequentially acquiring rotationally measured images, the unit rotation angle range being less than 180 degrees, and by applying the weight, it is possible to provide to the reconstructed image obtained from the rotationally measured images, the intensity variation equivalent to the reconstructed image obtained by the measurement using the rotation angle range of 180 degrees. The image processor 320 may also be provided a weight determiner (weight determining means) 322 configured to determine the weight. The image processor may also be provided with a display image generator (display image generating means) 324 configured to cut a tomographic image on an arbitrary plane, out of the reconstructed image and generate a display image. The arbitrary plane may be a plane being parallel to the surface along the bed on which the subject 104 is placed.

The converter 321 converts the measured images acquired by the measuring processor 310 into the rotationally measured images that are acquired when the X-ray source 101' and the detector 102' rotationally move along concentric circular paths about the rotation axis 106. In FIG. 3, the measuring processor 310 converts the measured images by moving the X-ray source 101 from the position A to the position B, and by moving the detector 102 from the position C to the position D, into the rotationally measured images acquired by rotationally moving the X-ray source 101' from the position A' to the position B', and by moving the detector 102' from the position C' to the position D'. When the converter 321 of the present embodiment converts the measured images into the rotationally measured images, the converter 321 simultaneously calculates the measurement angles of the respective rotationally measured images after the conversion.

Figure 7A:
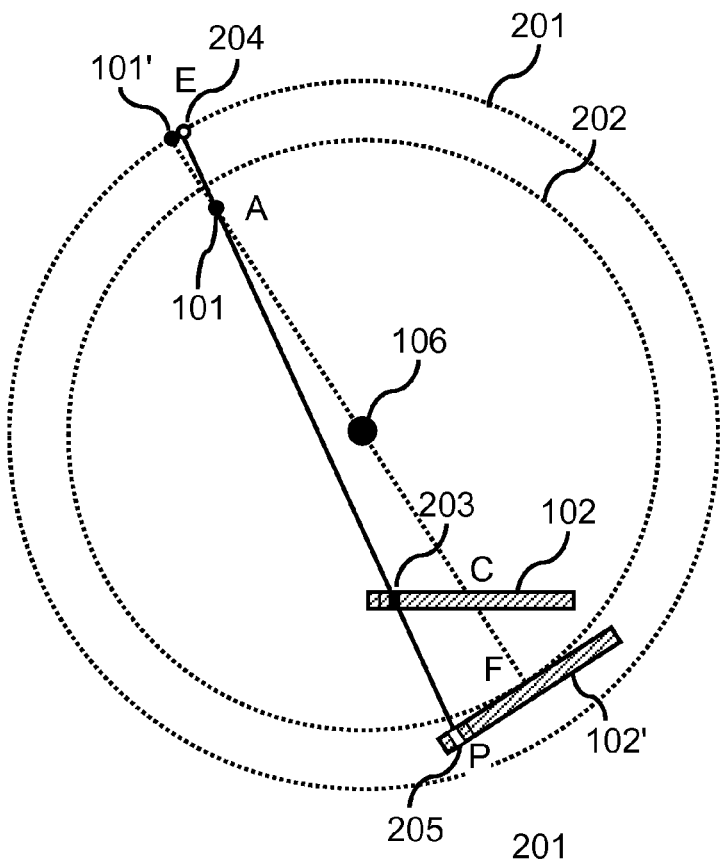
FIG. 7A illustrates a conversion process of the first embodiment.

The conversion is performed according to geometric transformation. In other words, the converter 321 converts the measured images into the rotationally measured images according to arithmetic operations including a processing of geometric transformation. FIG. 7A illustrates the conversion processing performed by the converter 321 of the present embodiment. The measured image obtained by the X-ray source 101 at the position A and the detector 102 at the position C is converted into the rotationally measured image obtained by the X-ray source 101' on the circular path 201 and by the detector 102' on the circular path 202, about the rotation axis 106. The X-ray beam generated from the X-ray source 101 enters detection element 203 on the detector 102. The position E is obtained where a line connecting the X-ray source 101 and the detection element 203 intersects the circular path 201. In addition, the position F, where a line connecting the X-ray source 101 and the rotation axis 106 intersects the circular path 202, is obtained. Then, the position P, where a line connecting X-ray source 101 and the detection element 203 intersects the tangent line at the position F on the circular path 202, is obtained.

The data obtained by the X-ray source 101 and the detection element 203 is converted into the data obtained by the X-ray source 204 at the position E and the detection element 205 at the position P on the detector 102' placed at the position F. Each radius of the concentric circular paths of the X-ray source 101' and the detector 102' as conversion targets, is determined in advance.

Figure 7B:
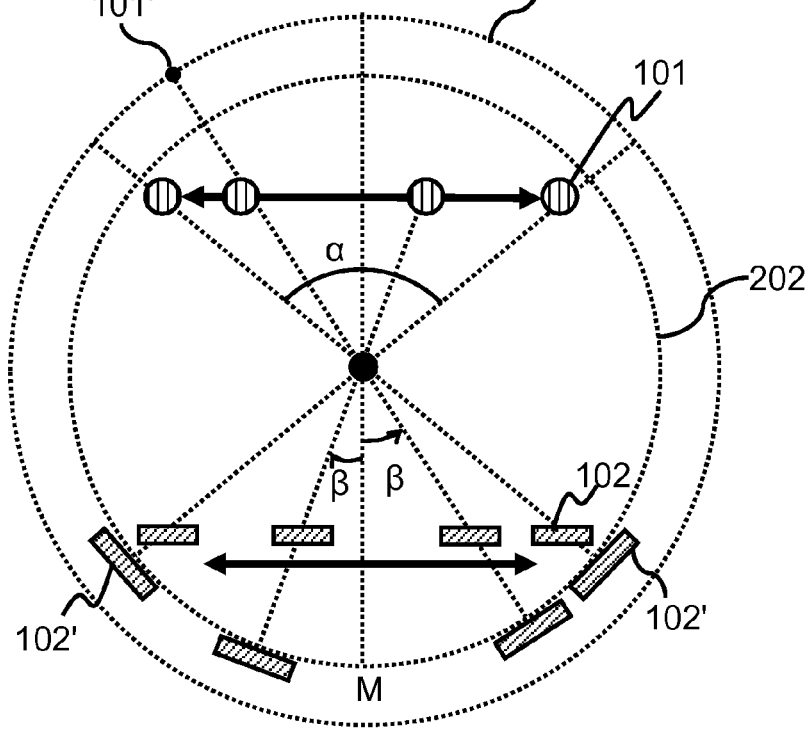
FIG. 7B illustrates a rotation angle range and a measurement angle of the first embodiment.

In the present specification, as shown in FIG. 7B, with regard to the rotationally measured images converted from the measured images, the central angle formed by the rotationally measured images at the detected positions on both edges is referred to as the "rotation angle range α", and the central angle formed between each of the rotationally measured images and the reference position M is referred to as the "measurement angle β" of each rotationally measured image.

The weight determiner 322 determines a weight responsive to the measurement angle, the weight being applied to the rotationally measured image. A weight decision process according to the weight determiner 322 of the present embodiment will be explained. The weight determiner 322 of the present embodiment determines the weight so that the reconstructed image from the rotationally measured images after the weights are applied thereon respectively, have intensity being equivalent to that of the reconstructed image obtained from the rotationally measured images when the rotation angle range is 180 degrees. This aims at forcing the structure in the periphery of the rotation angle range to undergo attenuation, as described above. Therefore, the weight determiner 322 determines the weight responsive to the measurement angle, in such a manner that as the measurement angle of the rotationally measured image comes closer to the edge of the rotation angle range, the intensity of the rotationally measured image is attenuated more. In other words, the weight is determined so that the intensity of the rotationally measured image become attenuated more, as the measurement angle of the rotationally measured image comes closer to the edge of the rotation angle range for the measurement to obtain one reconstructed image.

The weight responsive to the measurement angle may be a weight value by which each rotationally measured image is multiplied, for instance. As indicated by the weight variation profile 500 shown in FIG. 5, the weight value is maximized when applied to the rotationally measured image being the closest to the center of the rotation angle range targeted for the measurement, and the weight value becomes smaller as approaching the periphery of the rotation angle range. The weight determiner 322 extracts the rotation angle range α from the imaging condition set by an operator, and decides a variation profile of the weight (weight variation profile) responsive to the measurement angle. Then, when the converter 321 calculates the measurement angle of each of the rotationally measured images, the weight determiner decides the weight value to be applied to each of the rotationally measured images. It is to be noted that the maximum value and the minimum value of the weight variation profile are held in advance in the storage provided in the controller 103.

It is also possible that the weight value is determined as a function. In this function, the measurement angle is assumed as a variable, and the weight value becomes a maximum value at the center of the rotation angle range, a minimum value on both edges, and monotonically decreases from the center towards the edges. By way of example, a cubic function, a Sine function, or the like, may be employed.

The weight responsive to the measurement angle may be a size of the region where each rotationally measured image is smoothed. The size of the region to be smoothed is minimum when it is applied to the rotationally measured image being the closest to the center of the rotation angle range, and the size becomes larger as approaching the periphery of the rotation angle range. With this configuration, a blurred image is used at the angle on the periphery, and this may prevent occurrence of artifact caused by the images overlapping one another.

The weight determiner 322 extracts the rotation angle range α from the imaging condition set by the operator, and decides a variation profile (weight variation profile) of the smoothing region size responsive to the measurement angle. Then, when the converter 321 calculates the measurement angle as to each rotationally measured image, the weight determiner 322 decides the smoothing region size to be applied to each rotationally measured image. It is to be noted that the maximum value and the minimum value of the smoothing region size are held in advance in the storage that is provided in the controller 103.

Alternatively, the smoothing region size may be determined as a function. In this function, the measurement angle is assumed as a variable, and the size becomes a minimum value at the center of the rotation angle range, a maximum value on both edges, and monotonically increases from the center towards the edges. By way of example, a cubic function, a Sine function, or the like, may be employed.

The weight responsive to the measurement angle may be a maximum frequency that is allowed to pass through the reconstruction filter applied to each rotationally measured image. The reconstruction filter applied to the rotationally measured image, being the closest to the center of the rotation angle range, is formed in a shape allowing any frequency region up to the highest to pass through. On the other hand, as the rotationally measured image is closer the periphery of the rotation angle range, the filter is formed in such a manner that the higher frequency region is cut off.

With this configuration, an image from which detailed structures are removed is used at the peripheral angle, and this may prevent occurrence of artifact caused by the images overlapping one another.

The weight determiner 322 extracts the rotation angle range α from the imaging condition set by the operator, and determines a variation profile of maximum frequency (weight variation profile) responsive to the measurement angle, the maximum frequency being allowed to pass through the reconstruction filter. Then, when the converter 321 calculates the measurement angle as to each rotationally measured image, the weight determiner decides the maximum frequency allowed to pass through the reconstruction filter that is applied to each rotationally measured image. It is to be noted that the maximum value and the minimum value of the maximum frequency that is allowed to pass through the reconstruction filter are held in advance in the storage provided in the controller 103.

Figure 8:
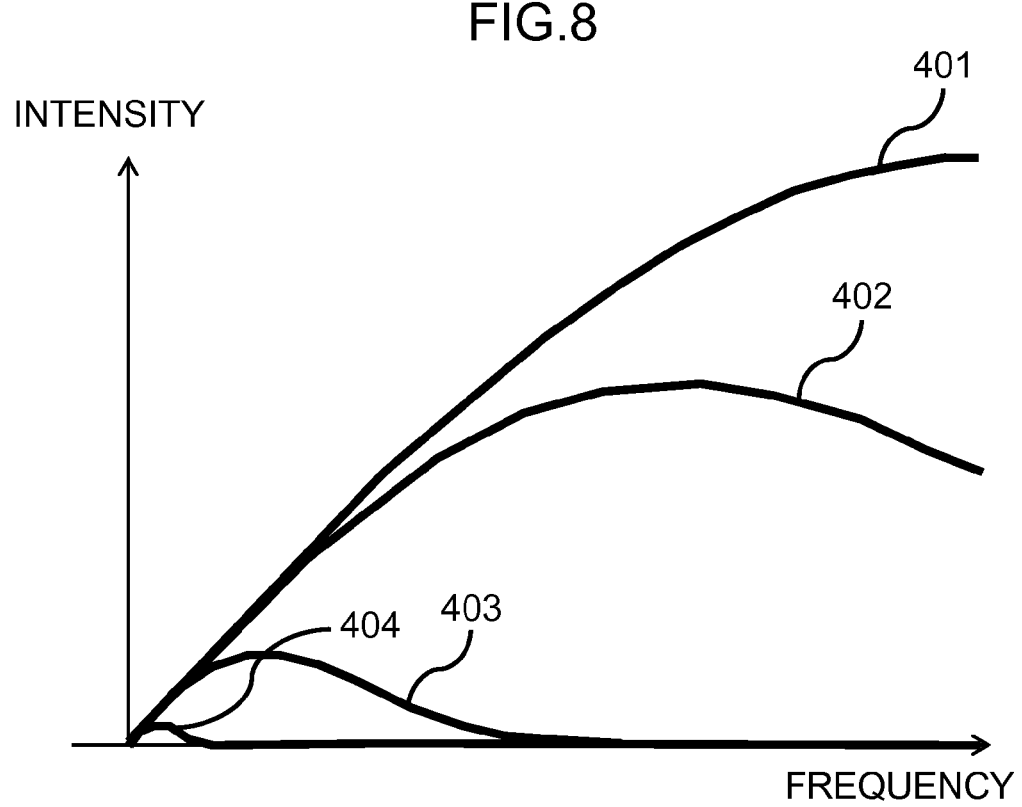
FIG. 8 illustrates a reconstruction filter of the first embodiment.

FIG. 8 shows specific examples of the reconstruction filter to be applied as the weight, with respect to each measurement angle. As shown in the figure, the reconstruction filter 401 applied to the rotationally measured image whose measurement angle is the closest to the center of the rotation angle range has the shape that enables usage of a high-frequency region. Then, as the measurement angle gets away from the center of the rotation angle range, the reconstruction filter is used in the order of 402 and 403, with the shape cutting off the high frequency region, and on both edges, the reconstruction filter 404 is utilized, having the shape that uses only a low frequency region.

The reconstructor 323 applies the weight decided by the weight determiner 322 to the rotationally measured image at every measurement angle, and performs a reconstruction operation to reconstruct a three-dimensional image. In the present embodiment, either of the back projection method and filtered back-projection method, being publicly known, may be employed as the reconstruction operation, for instance. Specifically, after applying the weights to the respective rotationally measured images, those images are added taking the measurement angles into account, and divided by the number of addition times, thereby obtaining a three-dimensional reconstructed image. It is assumed that the weight to be applied is at least one of the weight value, the smoothing region size, and the reconstruction filter.

The display image generator 324 generates an image (cross-sectional image or a tomographic image) to be displayed on the monitor that is connected to the X-ray imaging apparatus 120, from the three-dimensional constructed image that is generated by the reconstructor 323. Generally, the three-dimensional reconstructed image is obtained as accumulation of the cross-sectional images being perpendicular to the rotation axis 106. The display image generator 324 of the present embodiment applies a publicly known cutting-out process to the three-dimensional reconstructed image, and obtains a tomosynthesis image as a cross-sectional image being parallel to the rotation axis.

Figure 9:
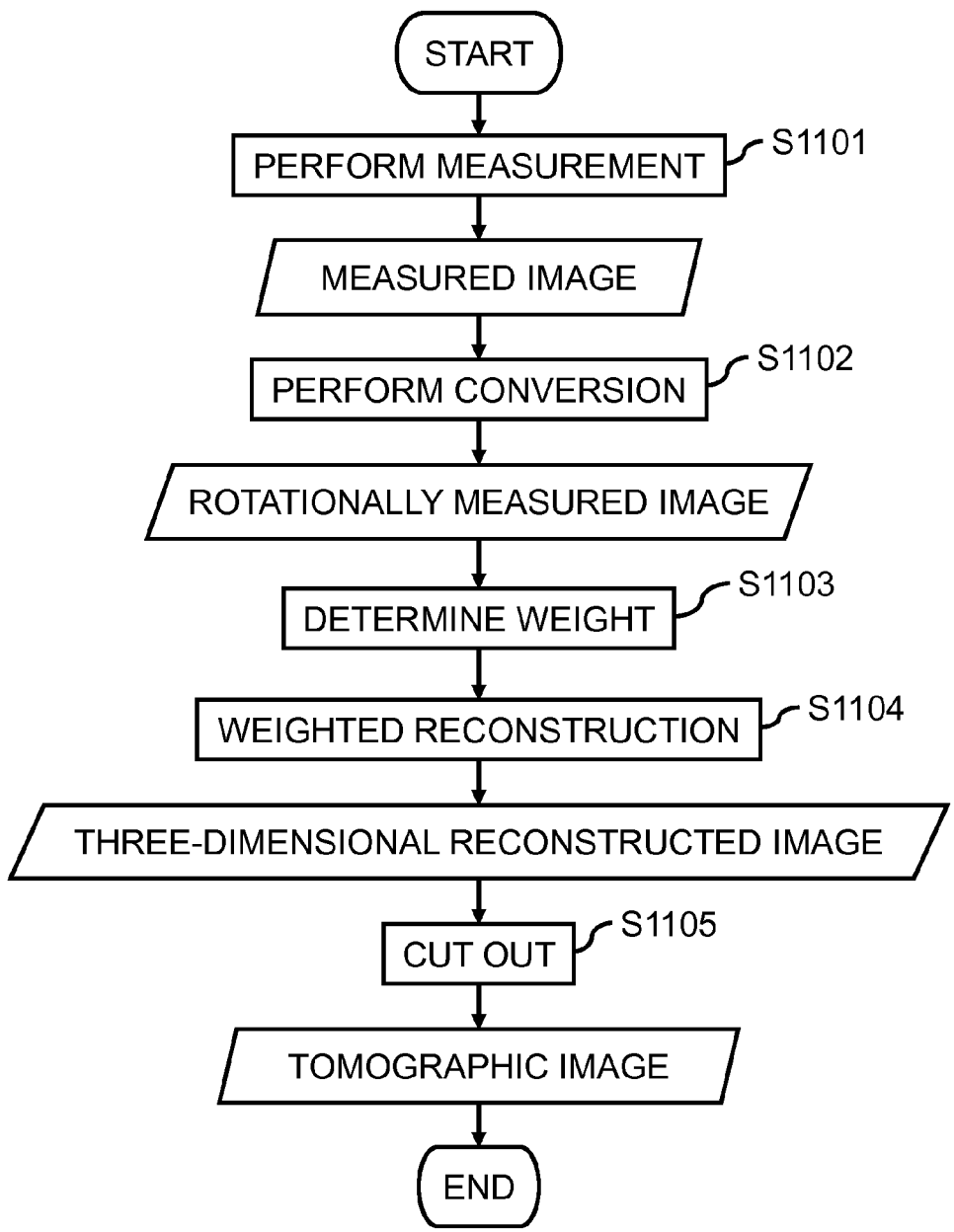
FIG. 9 is a flowchart showing the imaging process according to the first embodiment.

Hereinafter, a flow of the imaging process according to the controller 103 of the present embodiment will be explained. The imaging process converts the measured images into rotationally measured images acquired when the X-ray source 101 and the detector 102 rotationally move along the concentric circular paths, provides the rotationally measured images with weights so as to give the intensity variation to the reconstructed image obtained from the rotationally measured images, the intensity variation being equivalent to that of the reconstructed image obtained by the measurement with the rotation angle range of 180 degrees, performs the reconstruction operation, and obtains a reconstructed image. FIG. 9 is a processing flow of the imaging process according to the present embodiment. It is to be noted here that after the user sets the imaging condition, the weight determiner 322 decides in advance the weight variation profile regarding each measurement angle, by using the imaging condition. In the present embodiment, the weight determiner 322 decides as the weight, at least one of the following; the weight value, the smoothing region size, and the maximum frequency that is allowed to pass through the reconstruction filter.

The measuring processor 310 moves the X-ray source 101 and the detector 102 according to a predetermined program, causes the X-ray source 101 to emit X-rays, performs measurements (step S1101), and causes the detector 102 to acquire a measured image.

Next, the converter 321 converts thus obtained measured images into rotationally measured images that are obtained by the imaging apparatus in which the X-ray source 101 and the detector 102 rotationally move along the concentric circular paths (step S1102). In this situation, the converter 321 also calculates a measurement angle of each of the rotationally measured images after the conversion.

The weight determiner 322 determines a weight to be applied to each of the rotationally measured images, from the measurement angle being calculated (step S1103).

Then, the reconstructor 323 applies the weight to each of the rotationally measured images, performs a reconstruction operation (weighted reconstruction; step S1104), and a three-dimensional reconstructed image is obtained. The display image generator 324 cuts out an image of a desired cross section from the obtained three-dimensional reconstructed image (step S1105), displays the image on the monitor, for instance, and terminates the processing.

It is to be noted here that the weight to be applied to the rotationally measured image upon reconstruction, may be based on the weight value, the smoothing region size, or the reconstruction filter, and each of those may be used independently, or some of them may be combined.

The aforementioned processing flow is configured such that all the measured images in the rotation angle range are obtained, then similarly, rotationally measured images of all of those measured images are obtained, and thereafter, the reconstruction process is performed. However, this is not the only processing order. By way of example, every time the measured image is obtained, the rotationally measured image is obtained, and this process is repeated for all the measured images. Then, the reconstruction process may be performed after obtaining all the rotationally measured images in the rotation angle range are obtained.

It is also possible to configure such that every time the measured image is obtained, the rotationally measured image is obtained, then the weight is determined, and the weighted summation process is performed in the reconstruction process, taking the measurement angle into account. With this configuration, the memory for holding all the measured images and all the rotationally measured images in the rotation angle range is not necessary any more, thereby simplifying the configuration.

In the present embodiment, tomosynthesis imaging is taken as an example, but it is not the only example. By way of example, the angle range α may be 180 degrees or less in the CT imaging. In this case, the converter 321 uses the measured images being obtained as the rotationally measured images, without any change. In other words, the X-ray source 101 and the detector 102 relatively move, rotationally along the concentric circular paths, and the converter 321 assumes the measured images as the rotationally measured images.

In FIG. 3, the subject 104 is placed on the bed 105, and the body axis is assumed as being parallel with the floor on the paper surface. In this situation, when the installation state is the same as that of a general fluoroscopic imaging apparatus, it is possible to observe the left, right, top, and bottom of the obtained image, in the same manner as the fluoroscopic imaging apparatus. When the subject 104 is placed so that the body axis is perpendicular to the paper surface, the installation state becomes the same as that of a general CT scanner, and observation is possible as in the case of the CT image. It is further possible to arrange the body axis of the subject 104 in such a manner as perpendicular to the floor surface, just like turning the illustration of FIG. 3 by 90 degrees. In this case, the subject 104 is not lying on the bed 105, but in the state of sitting up or standing up. In this situation, when the X-ray source 101 and the detector 102 move in the direction perpendicular to the floor surface, observation is possible in the same manner as the fluoroscopic imaging apparatus. When the X-ray source 101 and the detector 102 move horizontally, observation is possible in the same manner as the CT image.

In the examples above, the body axis of the subject 104, the rotation axis of the X-ray source 101 and the detector 102, or the moving direction may be installed in a slanting direction with respect to the floor surface. With this configuration, a portion within the subject 104 being necessary for diagnosis is placed in such a manner as not overlapping another portion that is not required for the diagnosis, and this enables acquisition of a favorable image.

The relative movement of the X-ray source 101 and the detector 102 is not limited to the rotational movement and the linear movement. It is only required that the converter 321 is capable of performing conversion, according to the geometric transformation, into rotationally measured images that are obtained when the X-ray source 101 and the detector 102 rotationally move along the concentric circular paths about the rotation axis 106.

As described above, the X-ray imaging apparatus according to the present embodiment is provided with, the X-ray source 101 configured to irradiate the subject 104 with X-rays, the detector 102 configured to detect the X-rays, the measuring processor 310 configured to relatively move the X-ray source 101 and the detector 102 to acquire a measured image, and the image processor 320 configured to apply an arithmetic operation to the measured image so as to obtain an image, wherein the image processor 320 is provided with the converter 321 configured to convert the measured image into a rotationally measured image acquired in a predetermined rotation angle range when the X-ray source 101 and the detector 102 rotationally move along the concentric circular paths, and the reconstructor 323 configured to apply a weight to the rotationally measured image, the weight being responsive to the measurement angle of the rotationally measured image, perform a reconstruction operation, and obtain a reconstructed image, and the predetermined rotation angle range for acquiring the rotationally measured image includes at least one unit rotation angle range for sequentially acquiring the rotationally measured image, the unit rotation angle range is less than 180 degrees, and the weight provides the reconstructed image obtained from the rotationally measured images with intensity variation, the intensity variation being equivalent to that of the reconstructed image obtained by the measurement when the rotation angle range is 180 degrees.

In this situation, the weight may be determined so that the intensity of the weight for the rotationally measured image is attenuated more, as the measurement angle of the rotationally measured image comes closer to the edge of the rotation angle range used for the measurement to obtain one reconstructed image. The weight may be at least one of the following; the weight value by which the rotationally measured image at each measurement angle is multiplied, the region size for smoothing the rotationally measured image at each measurement angle, and the maximum frequency allowed to pass through the reconstruction filter that is applied to the rotationally measured image at each measurement angle.

The X-ray source 101 and the detector 102 may move in the direction along the bed 105 on which the subject 104 is placed, synchronously and in the directions opposite to each other, and the converter 321 may convert the measured image into the rotationally measured image, according to arithmetic operations including a geometric conversion process. The X-ray source 101 and the detector 102 may rotationally move relatively along the concentric circular paths, and the converter 321 assumes the measured image as the rotationally measured image.

The reconstruction operation may be either of the back projection method and the filtered back-projection method. The image processor 320 may be provided with the display image generator 324 configured to cut out a tomographic image of an arbitrary plane from the reconstructed image, and generate a display image. In addition, the arbitrary plane may be parallel to a surface along the bed on which the subject is placed.

The image processing method of the present embodiment performs imaging while moving the X-ray source and the detector relatively, the X-ray source being configured to irradiate a subject with X-rays and the detector being configured to detect the X-rays, and obtains a reconstructed image from a measured image being acquired, and the method converts the measured image into the rotationally measured image acquired in a predetermined rotation angle range when the X-ray source 101 and the detector 102 rotationally move along the concentric circular paths, provides the rotationally measured image with a weight that gives to the reconstructed image obtained from the rotationally measured images, intensity variation equivalent to that of the reconstructed image obtained by the measurement when the rotation angle range is 180 degrees, performs the reconstruction operation, obtains the reconstructed image, and assumes that the unit rotation angle range is less than 180 degrees, being the rotation angle range for sequentially obtaining the rotationally measured image.

Therefore, according to the present embodiment, the images obtained by the measurement using the rotation angle range being less than 180 degrees, if it is converted to the measurement along a rotation path, are converted so that the reconstruction image obtained from the measured images is provided with intensity variation equivalent to that of the reconstructed image obtained from the measured images that are acquired from the measurement using the rotation angle range being 180 degrees, and then, the reconstruction process is performed. With this configuration, it is possible to restrain occurrence of artifact that is caused by an insufficient rotation angle range in the reconstructed image. Therefore, even when only the measured images with the rotation angle range being less than 180 degrees are acquired, it is possible to obtain a reconstructed image and a cross-sectional image having the same quality as the reconstructed image that is obtained from the measured images acquired by the measurement using the range of 180 degrees.

By way of example, even when an image is acquired by the X-ray imaging apparatus for tomosynthesis imaging where the X-ray source 101 and the detector 102 move linearly in parallel with each other in the opposite directions, the quality of the image may be the same as the quality obtained by the reconstruction method similar to the CT scanner. Therefore, according to the reconstruction method similar to the CT scanner generally used, a cross-sectional image of the same quality may be obtained, irrespective of the layout, operations, and moving range of the X-ray source 101 and the detector 102. In other words, according to the present embodiment, even when the movement of the X-ray source 101 and the detector 102 is not a rotational movement, or irrespective of the moving paths, it is possible to obtain a reconstructed image with reduced artifact, using the images within the angle range less than 180 degrees, the artifact being caused by insufficient angle range. It is further possible to obtain a tomosynthesis image with less blurring and similar to a CT image.

Second Embodiment

Next, the second embodiment to which the present invention is applied will be explained. In the present embodiment, the weight which is applied to each rotationally measured image is optimized.

The X-ray imaging apparatus of the present embodiment is the same as the first embodiment. In other words, any of the apparatus as illustrated in the aforementioned FIG. 1A, FIG. 1B, and FIG. 1C may be applicable. Features of the respective constituents are basically the same. In the present embodiment, since the weight is optimized, the processing of the weight determiner 322 is different. Hereinafter, the present embodiment will be explained, focusing on the configuration that is different from the first embodiment.

Similar to the first embodiment, the weight determiner 322 of the present embodiment determines at least one of the weight value, the smoothing region size, the shape of the reconstruction filter, as the weight for each measurement angle, the weight being applied to the rotationally measured image. In this situation, the weight is configured to be changeable, and an evaluation value is set on the tomographic image that is finally obtained. Then, the weight determiner 322 repeats the reconstruction process and the cutout process, with changing the weight, and determines a value that optimizes the evaluation value as an optimum weight value. In the subsequent imaging, the optimum weight value being determined is assumed as the weight to employ. In this situation, the weight determiner 322 allows the reconstructor 323 and the display image generator 324 to perform the reconstruction process and the cutout process, respectively. In other words, the weight determiner 322 uses a predetermined evaluation value to optimize the weight.

By way of example, when a weight value by which each rotationally measured image is multiplied is used as the weight, the weight value is specified by a function having the measurement angle as a variable (weight value decision function). Here, it is assumed that the weight value decision function takes the value of 1.0, at the center of the rotation angle range, and the value of 0.0 on both edges of the rotation angle range. By way of example, a cubic function, a Sine function, or the like, may be employed as the weight value decision function. As the evaluation value, a statistical value of the pixel values in a predetermined region of the tomographic image may be used. The statistical value to be used may be, for instance, a variance, a mean value, a maximum value, a minimum value, a median value, a degree of sharpness, or the like. By way of example, the region is set on a site that does not include a steep structure, such as a lung field and a liver. Then, a coefficient of the weight value decision function is varied, and a reconstructed image and a tomographic image are obtained for each coefficient, thereby calculating the evaluation value. At this timing, a weight value obtained by the weight value decision function that uses the coefficient rendering the evaluation value to be a minimum or a local minimum, is assumed as the optimum weight value.

In this situation, the evaluation function may be determined, assuming the coefficient of the weight value decision function as the horizontal axis, and the evaluation value as the vertical axis, and a coefficient that allows the evaluation function to take a minimum or a local minimum may be assumed as the coefficient to obtain the optimum weight value.

It is further possible that the region is set at a site that includes a steep structure such as bones like costal bone and spine, and blood vessels, and the statistical value in the region may be used as the evaluation value. Here, a coefficient that renders the evaluation value to be a maximum or a local maximum is assumed as the coefficient for obtaining the optimum weight value. Alternatively, the evaluation function is determined, assuming the coefficient as the horizontal axis and the evaluation value as the vertical axis, and a coefficient that renders the evaluation function to be a maximum or a local maximum may be assumed as the coefficient to obtain the optimum weight value.

By way of example, when the size of the smoothing region is used as the weight, the function that uses the measurement angle as a variable and returns a pixel count is assumed as the region size decision function. When the measurement angle is at the center of the rotation angle range, this region size decision function returns a value indicating the region size of 1×1 pixel, for instance, and when the measurement angle is at any of both edges of the rotation angle range, the region size decision function returns a value indicating the region size of 20×20 pixels. By way of example, a cubic function, a Sine function, or the like, may be employed as the region size decision function. A method for obtaining an optimum size is the same as the method of the case where the weight value is used.

The optimization may be performed not only by changing the size, but also by changing the shape of the smoothing region. By way of example, the optimization may be performed by changing the smoothing region to be vertically long, thereby extracting a structure such as a blood vessel that extends in the lateral direction. As the region size decision function, it is possible to employ a function that is able to perform optimization taking the shape into account, depending on the structure demanded to be extracted.

By way of example, when the reconstruction filter is varied, being used as the weight, a function using the measurement angle as a variable and returning a relative value of the maximum frequency allowed to pass through, is assumed as a frequency decision function. When the measurement angle is at the center of the rotation angle range, this frequency decision function allows all the frequencies to pass through, for instance, and when the measurement angle is at any of both edges of the rotation angle range, the frequency decision function returns a value indicating that the maximum frequency allowed to pass through is 1/32 of the maximum frequency for the case that the measurement angle is at the center. By way of example, the frequency decision function assumes the measurement angle as the horizontal axis, and a relative value of the maximum frequency with respect to the frequency to pass through in the case where the measurement angle is at the center of the rotation angle range, as the vertical axis, and the frequency decision function may be approximated by a cubic function, a Sine function, or the like.

Also in the case where the reconstruction filter is used, the filter is formed in a shape to cut the high frequency in the longitudinal direction not in the lateral direction, thereby extracting a structure such as a blood vessel extending in the lateral direction. Therefore, as the frequency decision function, it is possible to set a function taking the direction into account, so as to perform optimization depending on the structure demanded to extract.

Figure 10:
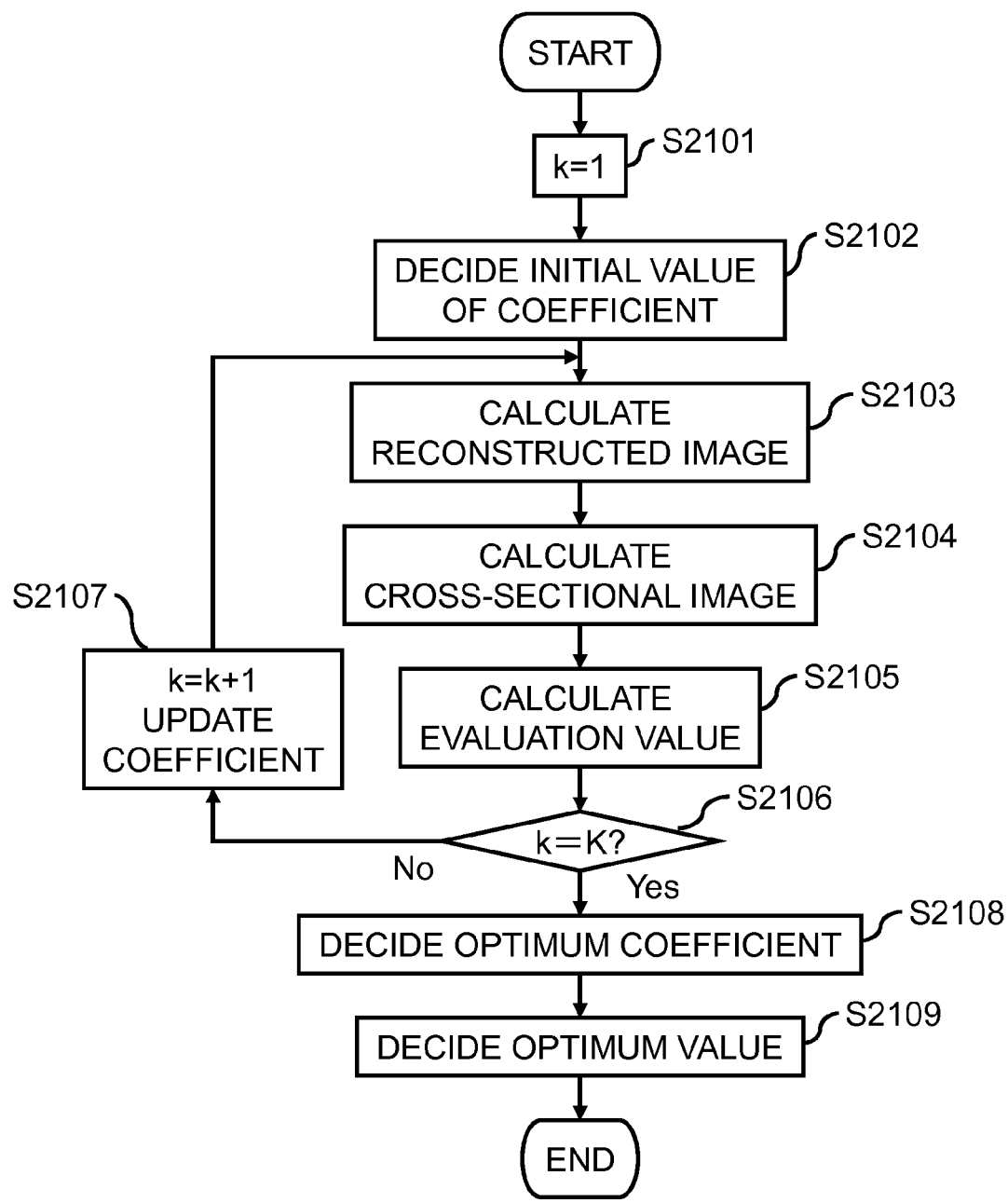
FIG. 10 is a flowchart showing the weight decision process according to the second embodiment.

A weight decision process according to the weight determiner 322 of the present embodiment will be explained. FIG. 10 is a processing flow of the weight decision process of the present embodiment. Here, it is assumed that all the rotationally measured images are obtained in advance, from all the measured images within a predetermined rotation angle range. It is also assumed that a profile of the weight value decision function, a change amount of the coefficient, and the number of changes K are predetermined, and stored in the storage device.

After the imaging condition is defined, the weight determiner 322 sets the counter k to 1 (step S2101), and determines the weight variation profile regarding each of the measurement angles to be applied respectively to the rotationally measured images, according to the method of the first embodiment, and decides an initial value of the coefficient of the weight value decision function (step S2102). It is to be noted that the initial value of the coefficient is assumed as the coefficient when k=1 (the first coefficient).

The weight determiner 322 allows the reconstructor 323 to calculate a three-dimensional reconstructed image, by using the weight specified by the k-th coefficient (step S2103). The weight determiner further allows the display image generator 324 to calculate a cross-sectional image of a predetermined cross section (step S2104). Then, the weight determiner 322 calculates the k-th evaluation value (step S2105). The k-th evaluation value being calculated is held in the storage device, and the like, in association with the k-th coefficient.

Then, it is judged whether or not the processing above is repeated K times (step S2106), and if it is less than K times, the coefficient is updated to a value changed only by a predetermined amount, simultaneously incrementing the counter k by 1 (step S2107), and the processing returns to the step S2103.

In the step S2106, if it is judged that the processing is repeated K times, the weight determiner 322 decides an optimum coefficient from the K evaluation values (step S2108), and further decides an optimum weight value (step S2109). It is to be noted that a minimum (or maximum) evaluation value is specified from the K evaluation values, and a coefficient that is associated with the evaluation value is assumed as the optimum coefficient.

The weight decision process for determining the optimum weight is not limited to the aforementioned method. It is possible to apply various publicly known optimization method.

It is to be noted here that the measurement process of the measuring processor 310, and the processing of reconstructor 323 and the display image generator 324 after the weight is determined by the weight determiner 322 of the present embodiment are the same as those of the first embodiment.

Also in the present embodiment, at least one of the weight value, the smoothing region size, and the reconstruction filter shape may be used as the weight.

Also in the present embodiment, the X-ray imaging apparatus is only required to acquire the measured image that the converter 321 is able to convert into the rotationally measured image being acquired by an apparatus in which the X-ray source 101 and the detector 102 rotationally move along the concentric circular paths about the rotation axis 106, and any layout, operations, and moving ranges of the X-ray source 101 and the detector 102 are acceptable.

As explained above, the X-ray imaging apparatus of the present embodiment is provided with the X-ray source 101 configured to irradiate the subject 104 with X-rays, the detector 102 configured to detect the X-rays, the measuring processor 310 configured to relatively move the X-ray source 101 and the detector 102 to obtain a measured image, and the image processor 320 configured to apply an arithmetic operation on the measured image to obtain an image, wherein the image processor 320 is provided with the converter 321 configured to convert the measured image into a rotationally measured image being acquired in a predetermined rotation angle range, when the X-ray source 101 and the detector 102 move rotationally along the concentric circular paths, and the reconstructor 323 configured to apply a weight to the rotationally measured image, the weight being responsive to a measurement angle of the rotationally measured image, perform the reconstruction operation, and obtain a reconstructed image, the predetermined rotation angle range for acquiring the rotationally measured image including at least one unit rotation angle range for sequentially acquire the rotationally measured images, the unit rotation angle range being less than 180 degrees, and the weight provides the reconstructed image obtained from the rotationally measured images, with intensity variation equivalent to that of the reconstructed image obtained by the measurement using the rotation angle range of 180 degrees.

In this situation, the weight may be determined in such a manner that the intensity of the weight for the rotationally measured image is attenuated more, as the measurement angle of the rotationally measured image comes closer to the edge of the rotation angle range for the measurement to obtain one reconstructed image. The image processor 320 may further be provided with the weight determiner 322 configured to determine the weight, and the weight determiner 322 may use a predetermined evaluation value to optimize the weight. The weight may be at least one of the weight value by which the rotationally measured image at each measurement angle is multiplied, the region size for smoothing the rotationally measured image at each measurement angle, and a maximum frequency that is allowed to pass through the reconstruction filter applied to the rotationally measured image at each measurement angle.

The X-ray source 101 and the detector 102 move synchronously and in the directions opposite to each other, along the bed 105 on which the subject 104 is placed, and the converter 321 may convert the measured image into the rotationally measured image, according to arithmetic operations including a geometric transformation process. The X-ray source 101 and the detector 102 may rotationally move along the concentric circular paths relatively, and the converter 321 may assume the measured image as the rotationally measured image.

The reconstruction operation may be any of the back projection method and the filtered back-projection method. The image processor 320 may further be provided with the display image generator 324 configured to cut out a tomographic image of an arbitrary plane from the reconstructed image, and generate a display image. The arbitrary plane may be a plane parallel to the surface along the bed on which the subject is placed.

Furthermore, the image processing method of the present embodiment performs imaging while moving the X-ray source and the detector relatively, the X-ray source being configured to irradiate a subject with X-rays and the detector being configured to detect the X-rays, and obtains a reconstructed image from a measured image being acquired, and the method converts the measured image into a rotationally measured image acquired in a predetermined rotation angle range when the X-ray source 101 and the detector 102 rotationally move along the concentric circular paths, provides the rotationally measured image with a weight that gives to the reconstructed image obtained from the rotationally measured images, intensity variation equivalent to that of the reconstructed image obtained by the measurement when the rotation angle range is 180 degrees, performs the reconstruction operation, obtains the reconstructed image, and assumes the unit rotation angle range is less than 180 degrees, being the rotation angle range for sequentially obtaining the rotationally measured images.

Therefore, according to the reconstruction method in the same manner as the CT scanner generally used, similar to the first embodiment, a cross-sectional image of the same quality may be obtained, irrespective of the layout, operations, and moving range of the X-ray source and the detector. In addition, according to the present embodiment, the weight is optimized. Therefore, the optimization enables obtaining of the most favorable cross-sectional image, in response to the imaging target and imaging conditions. In addition, the evaluation function is used, and accordingly, the optimization is performed automatically. This configuration may achieve less burden on the operator.

Third Embodiment

Next, the third embodiment to which the present invention is applied will be explained. In the present embodiment, the measurement of the predetermined rotation angle range (unit rotation angle range) being less than 180 degrees may be performed repeatedly. Within each unit rotation angle range, the measured image is sequentially obtained at every predetermined measurement angle. In other words, in the present embodiment, the measurement for obtaining one reconstructed image is performed more than once, in association with different rotation angle ranges. In the present embodiment, an image is reconstructed for each unit rotation angle range. The weight is determined for each unit rotation angle range, according to the method similar to the first embodiment. The unit rotation angle ranges for acquiring the measured images are not necessarily continuous.

The X-ray imaging apparatus of the present embodiment is basically the same as that of the first embodiment. The measurement process by the measuring processor 310 is different. Hereinafter, the present embodiment will be explained focusing on the configuration different from the first embodiment. In the present embodiment, the case where the radiation imaging apparatus in which the X-ray source 101 and the detector 102 move rotationally along the concentric circular paths about the rotation axis 106 is used will be explained.

Hereinafter, the measurement process according to the measuring processor 310 of the present embodiment will be explained. The measuring processor 310 of the present embodiment performs measurement of one or more predetermined unit rotation angle ranges. In the measurement within one unit rotation angle range, similar to the first embodiment, the measured image is obtained at every predetermined measurement angle.

Figure 11:
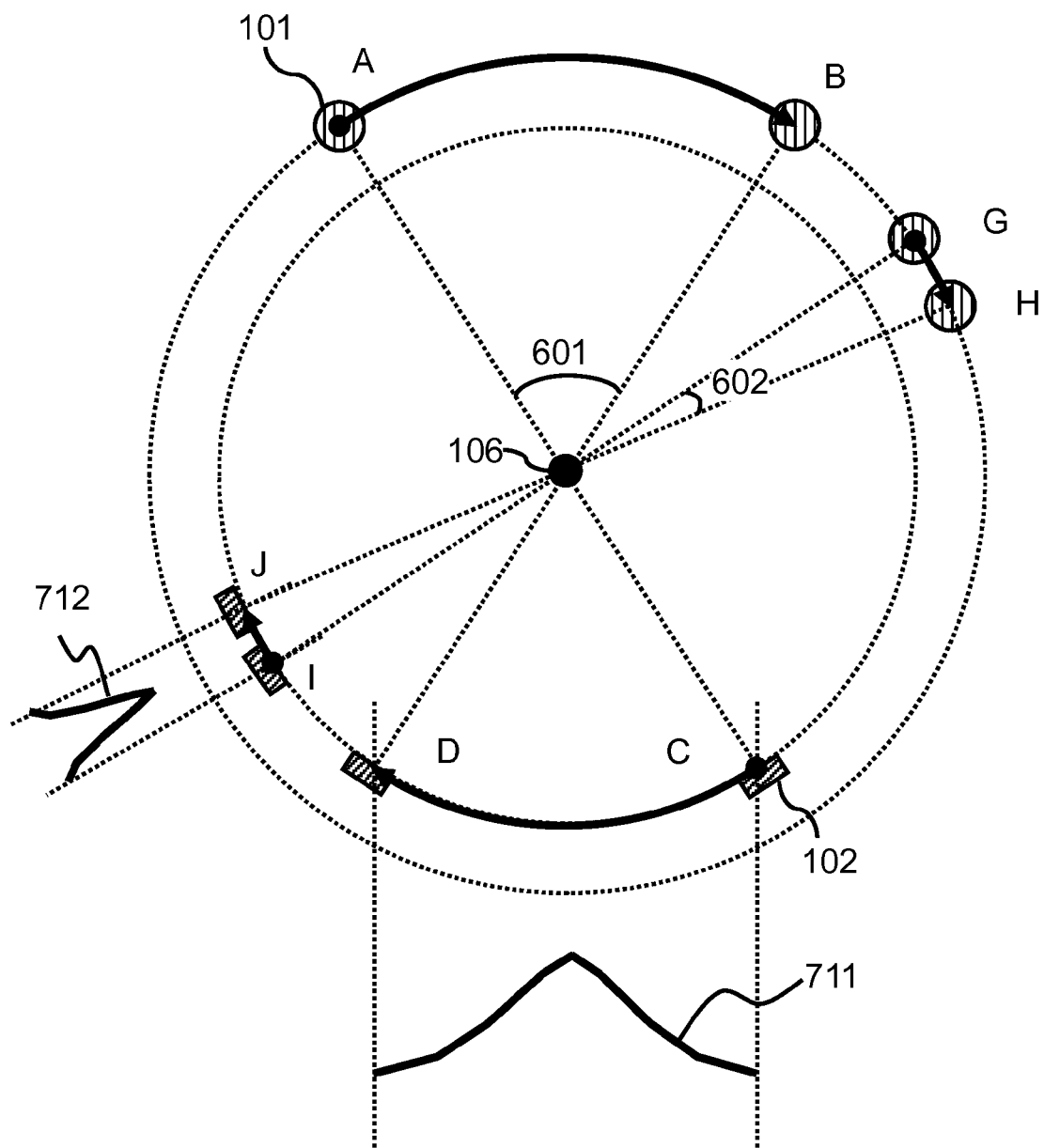
FIG. 11 illustrates the measurement range and the profile of the weight according to the third embodiment.

FIG. 11 illustrates a specific example. In the example being illustrated, the measuring processor 310 performs measurement of two unit rotation angle ranges; the first unit rotation angle range 601 in which the X-ray source 101 rotationally moves from the position A from the position B, and the second unit rotation angle range 602 in which the X-ray source 101 rotationally moves from the position G to the position H, and obtains the measured image at every measurement angle, in each of the two ranges. In this situation, the detector 102 rotationally moves from the position C to the position D and from the position I to the position J, in the two ranges, respectively.

The weight determiner 322 of the present embodiment determines the weight as to each of the unit rotation angler range, according to a method similar to the first embodiment.

By way of example, the profile of the weight variation (weight variation profile) regarding each measurement angle applied to the measured images (rotationally measured images) obtained in the first unit rotation angle range 601 (the detector moves from the position C to the position D), and the weight variation profile regarding each measurement angle applied to the rotationally measured images obtained in the second unit rotation angle range 602 (the detector moves from the position I to the position J), are respectively represented by the graph 711 and the graph 712 in FIG. 11. Similar to the first embodiment, it is assumed that any of the above variation profiles takes a maximum value at the center of the unit rotation angle range, and decreases monotonously towards both edges of the unit rotation angle range.

It is to be noted that the processes in the respective parts after the measuring processor 310 acquires the measured images (rotationally measured images) in each of the unit rotation angle ranges are the same as that of the first embodiment. In other words, similar to the first embodiment, the converter 321 converts the measured image into the rotationally measured image, every time the measuring processor 310 acquires the measured image in the predetermined unit rotation angle range. The reconstructor 323 applies the weight determined by the weight determiner 322 to each of the rotationally measured images, and obtains a three-dimensional reconstructed image. Then, the display image generator 324 obtains a desired cross-sectional image.

Figure 12:
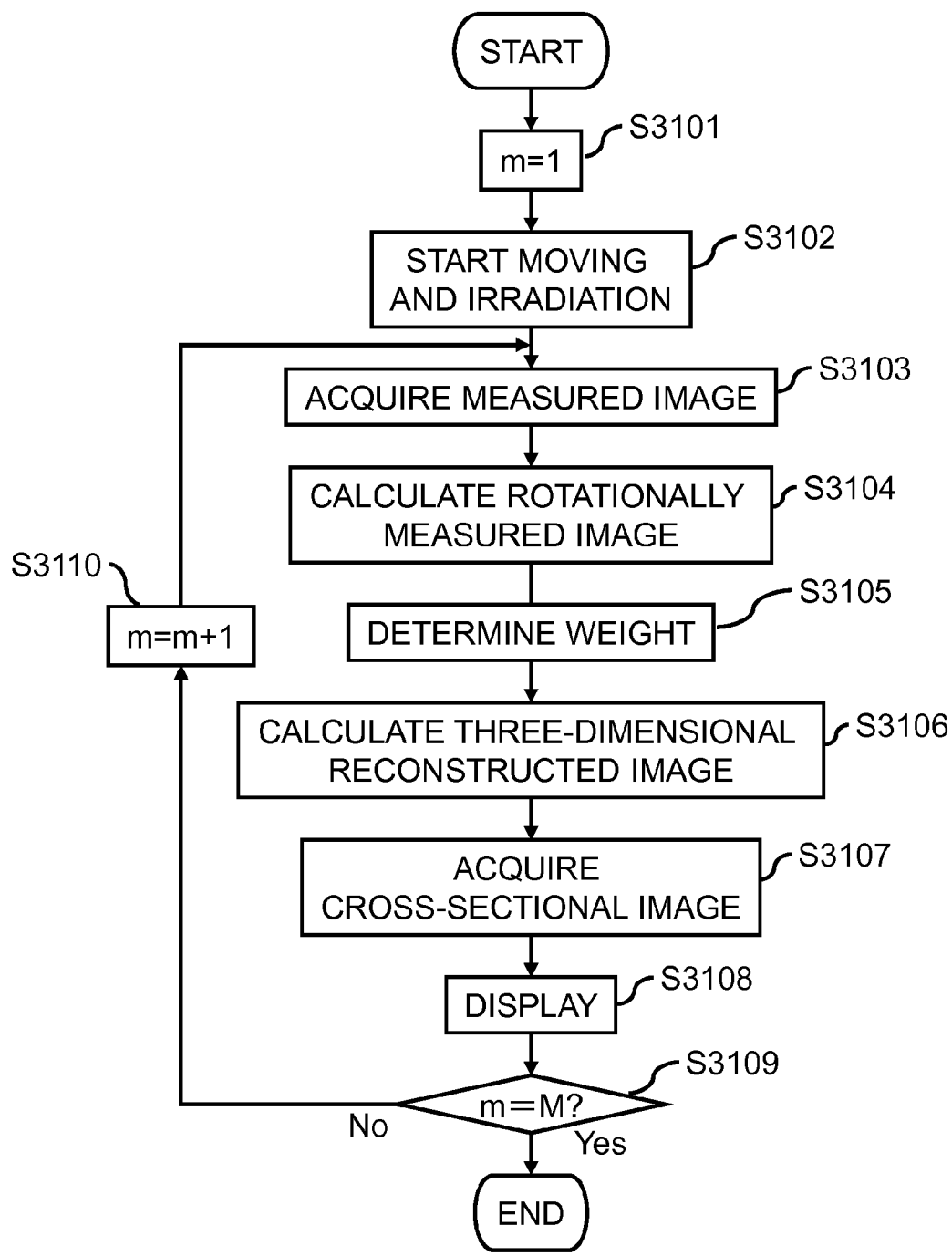
FIG. 12 is a flowchart showing the imaging process of the third embodiment.

Hereinafter, a flow of the imaging process according to the controller 103 of the present embodiment will be explained. FIG. 12 is a processing flow of the imaging process according to the present embodiment. Here, the measuring processor 310 performs measurement of M regions (unit rotation angle ranges), each of which has the rotation angle range being less than 180 degrees. Here, m represents a counter. It is assumed here that the weight for each measurement angle, in each of the regions, is determined in advance by the weight determiner 322. Here, an example will be explained, where the measuring processor 310 obtains a three-dimensional reconstructed image and a cross-sectional image every time obtaining the measured images within one unit rotation angle range, and a series of cross-sectional images are displayed sequentially along the time flow.

The measuring processor 310 initializes the counter m (step S3101). The measuring processor 310 starts the rotational movement of the X-ray source 101 and the detector 102, and radiation of X-rays (step S3102). Then, the measuring processor 310 acquires the measured images in a predetermined m-th unit rotation angle range (step S3103). In receipt of the measured images, the converter 321 calculates rotationally measured images and the measurement angles (step S3104). The weight determiner 322 determines the weights to be applied to the rotationally measured images (step S3105).

The reconstructor 323 uses the method of the first embodiment, and obtains the three-dimensional reconstructed image of the m-th unit rotation angle range (step S3106). The display image generator 324 obtains a cross-sectional image of a predetermined plane, in the m-th unit rotation angle range (step S3107), and displays the cross-sectional image on the monitor (step S3108).

The measuring processor 310 repeats the processes from the step S3103 to the step S3108, until reaching the M-th unit rotation angle range (steps S3109 and S3110).

Also in the present embodiment, the weight to be applied to the rotationally measured image when reconstruction is performed, may be based on at least one of the following; the weight value, the smoothing region size, and the reconstruction filter.

Also in the present embodiment, similar to the first embodiment, after all the measured images in one rotation angle range are obtained, rotationally measured images of all the measured images within this unit rotation angle range are obtained, and then, the reconstruction process is performed. However, the processing is not limited to this order. By way of example, every time the measured image is obtained, the rotationally measured image is obtained, and this is repeated for all the measured images within one unit rotation angle range. Then, the reconstruction process may be performed after obtaining all the rotationally measured images within the unit rotation angle range.

It is further possible to configure such that every time the measured image is obtained at each measurement angle, the rotationally measured image is obtained, the weight is determined, and the weighted summation process of the reconstruction process is performed, taking the measurement angle into account. With this configuration, the memory for holding all measured images and all rotationally measured images of one unit rotation angle range is not necessary any more, thereby simplifying the configuration.

Also in the present embodiment, the X-ray imaging apparatus 120 is only required to acquire measured images that the converter 321 is able to convert into rotationally measured images being acquired by an apparatus in which the X-ray source 101 and the detector 102 rotationally move along the concentric circular paths about the rotation axis 106, and any layout, operations, and moving ranges of the X-ray source 101 and the detector 102 are applicable.

As explained above, the X-ray imaging apparatus according to the present embodiment is provided with, the X-ray source 101 configured to irradiate the subject 104 with X-rays, the detector 102 configured to detect the X-rays, the measuring processor 310 configured to relatively move the X-ray source 101 and the detector 102 to acquire a measured image, and the image processor 320 configured to apply an arithmetic operation to the measured image so as to obtain an image, wherein the image processor 320 is provided with the converter 321 configured to convert the measured image, into a rotationally measured image acquired in a predetermined rotation angle range when the X-ray source 101 and the detector 102 rotationally move along the concentric circular paths, and the reconstructor 323 configured to apply a weight to the rotationally measured image, responsive to the measurement angle of the rotationally measured image, perform a reconstruction operation, and obtain a reconstructed image, and the predetermined rotation angle range for acquiring the rotationally measured image includes at least one unit rotation angle range for sequentially acquiring the rotationally measured images, the unit rotation angle range is less than 180 degrees, and the weight provides the reconstructed image obtained from the rotationally measured images with intensity variation being equivalent to that of the reconstructed image that is obtained by the measurement when the rotation angle range is 180 degrees.

The weight may be determined in such a manner that as the measurement angle of the rotationally measured image comes closer to the edge of the rotation angle range of the measurement for obtaining one reconstructed image, the intensity is attenuated more. In addition, the weight may be determined in such a manner that the intensity of the weight is attenuated more, as the measurement angle of the rotationally measured image comes closer to the edge of the unit rotation angle range. Furthermore, the measurement for obtaining one reconstructed image, being associated with a different rotation angle range, may be performed more than once. The image processor 320 is further provided with the weight determiner 322 configured to determine the weight, and the weight determiner 322 may use a predetermined evaluation value so as to optimize the weight. The weight may be at least one of the following; the weight value by which the rotationally measured image at each measurement angle is multiplied, the region size for smoothing the rotationally measured image at each measurement angle, and the maximum frequency allowed to pass through the reconstruction filter, being applied to the rotationally measured image at each measurement angle.

The X-ray source 101 and the detector 102 move synchronously in the directions opposite to each other, along the bed 105 on which the subject 104 is placed, and the converter 321 may convert the measured image into the rotationally measured image, according to the arithmetic operations including the geometric transformation process. The X-ray source 101 and the detector 102 relatively move rotationally along the concentric circular paths, and the converter 321 may assume the measured image as the rotationally measured image. The reconstruction operation may be any of the back projection method and the filtered back-projection method. The image processor 320 may further be provided with the display image generator 324 configured to cut out a tomographic image of an arbitrary plane from the reconstructed image, and generate a display image. The arbitrary plane may be a plane parallel to the surface along the bed on which the subject 104 is placed.

Furthermore, the image processing method that performs imaging while moving the X-ray source and the detector relatively, the X-ray source being configured to irradiate a subject with X-rays and the detector being configured to detect the X-rays, and obtains a reconstructed image from a measured image being acquired, and the method converts the measured image into the rotationally measured image acquired in a predetermined rotation angle range when the X-ray source 101 and the detector 102 rotationally move along the concentric circular paths, provides the rotationally measured image with a weight that gives to the reconstructed image obtained from the rotationally measured images, intensity variation equivalent to that of the reconstructed image obtained by the measurement when the rotation angle range is 180 degrees, performs the reconstruction operation, obtains the reconstructed image, and assumes the unit rotation angle range is less than 180 degrees, being the rotation angle range for sequentially obtaining the rotationally measured images.

Therefore, in the present embodiment similar to the first embodiment, according to the reconstruction method in the same manner as a CT scanner generally used, a cross-sectional image of the same quality may be obtained, irrespective of the layout, operations, and moving range of the X-ray source and the detector.

Further according to the present embodiment, the unit rotation angle range is defined every predetermined period of time, and processing is repeated, thereby obtaining images (e.g., tomosynthesis images) at established intervals. These series of images are sequentially displayed along the time flow, and it is possible to observe temporal variation. By way of example, this processing may be performed during angiography, and temporal variation of the angiography may be observed.

Since the unit rotation angle range is defined in sync with a body motion, an image with low artifact may be obtained, even when a portion with a large body motion is targeted for imaging. It is alternatively possible to present the variation in association with the body motion.

By way of example, plural angle ranges in the heart's diastole phase are selected, and when each of the ranges is assumed as the unit rotation angle range, and the measurement and the image processing of the present embodiment are performed, an image in the diastole phase is obtained. Similarly, plural angle ranges in the heart's systolic phase are selected, and when each of the ranges is assumed as the unit rotation angle range, and the measurement and the image processing of the present embodiment are performed, an image in the systolic phase is obtained. With this configuration, it is possible to reduce the artifact caused by the effect of heart beats.

By way of example, plural angle ranges in the state of expiration are selected, and each of the ranges is assumed as the unit rotation angle range. Then, when the imaging and image processing of the present embodiment are performed, it is possible to obtain an image at the time of expiration. Similarly, plural angle ranges in the state of inspiration are selected, and each of the ranges is assumed as the unit rotation angle range. Then, when the imaging and image processing of the present embodiment are performed, it is possible to obtain an image at the time of inspiration. With this configuration, artifact caused by respiration may be reduced.

Alternatively, the motion of the subject is detected by using an index such as a bone or a marker, and plural angle ranges without motion are selected, and each of the ranges is assumed as the unit rotation angle range. Then, when the imaging and image processing of the present embodiment are performed, it is possible to obtain an image being motionless. Similarly, plural angle ranges going through the same motion are selected, and each of the ranges is assumed as the unit rotation angle range. Then, when the imaging and image processing of the present embodiment are performed, it is possible to obtain an image going through the same motion. With this configuration, artifact caused by the motion of the subject may be reduced.

By way of example, when the tomosynthesis imaging is performed, the tomosynthesis image obtained at each of the unit rotation angle ranges is assumed as an image viewed from the center angle of each unit rotation angle range.

Accordingly, it is possible to obtain the tomosynthesis image with a favorable image quality being balanced between left and right. In addition, the tomosynthesis images obtained at each of the unit rotation angle ranges is assumed as being viewed from the same rotation angle. With this configuration, it is possible to display the tomosynthesis image viewed from the same direction constantly.

According to the present embodiment, the weights responsive to the weight variation profile similar to the first embodiment are applied to the respective rotationally measured images in each of the unit rotation angle ranges. Therefore, even when there is large distance between the defined plural unit rotation angle ranges (between the first unit rotation angle range and the second unit rotation angle range), it is possible to prevent occurrence of artifacts in the reconstructed image, thereby obtaining a high-quality image.

In the present embodiment, an example is explained where the unit rotation angle range is defined in advance for acquiring measured images, but this is not the only example. By way of example, it may be configured such that each of the X-ray imaging apparatus 110, 120, and 130 is provided with a biological monitor, or the like, and the measuring processor 310 determines an acquisition timing.

In the present embodiment, a specific example is explained, where the number of the unit rotation angle ranges is two. However, the number of the unit rotation angle ranges is not limited to two, but any number is applicable. It is further possible that plural rotationally measured images are obtained at the position of the same rotation angle after converted to the circular path, such as the case where the imaging is performed repeatedly. In this situation, the weight applied to each of the plural rotationally measured images obtained at the same position is assumed as a value obtained by dividing the calculated weight value by the number of the rotationally measured images overlapping one another.

Fourth Embodiment

Next, the fourth embodiment to which the present invention is applied will be explained. In the present embodiment, similar to the third embodiment, measurement of the predetermined unit rotation angle range being less than 180 degrees is repeatedly performed. Within each of the unit rotation angle range, measured images are sequentially obtained at predetermined measurement angles, respectively. In the present embodiment, however, one image is reconstructed from the measured images obtained in the plural unit rotation angle ranges. It is to be noted that the unit rotation angle ranges for acquiring the measured images are not necessarily continuous.

The X-ray imaging apparatus of the present embodiment is basically the same as that of the first embodiment. In the present embodiment, one reconstructed image is obtained from the rotationally measured images in plural unit rotation angle ranges, and therefore, the weight variation profile determined by the weight determiner 322 is different. Since the rotationally measured images to be obtained are associated with the plural unit rotation angle ranges, the processing in the measuring processor 310 is also different. Hereinafter, the present embodiment will be explained, focusing on the configuration different from the first embodiment. In the present embodiment, an explanation will be made as to using the radiation imaging apparatus in which the X-ray source 101 and the detector 102 rotationally move along the concentric circular paths about the rotation axis 106.

The measuring process according to the measuring processor 310 of the present embodiment is basically the same as the measuring process of the third embodiment. In other words, the measured images are acquired in one or more unit rotation angle ranges being predetermined.

Figure 13:
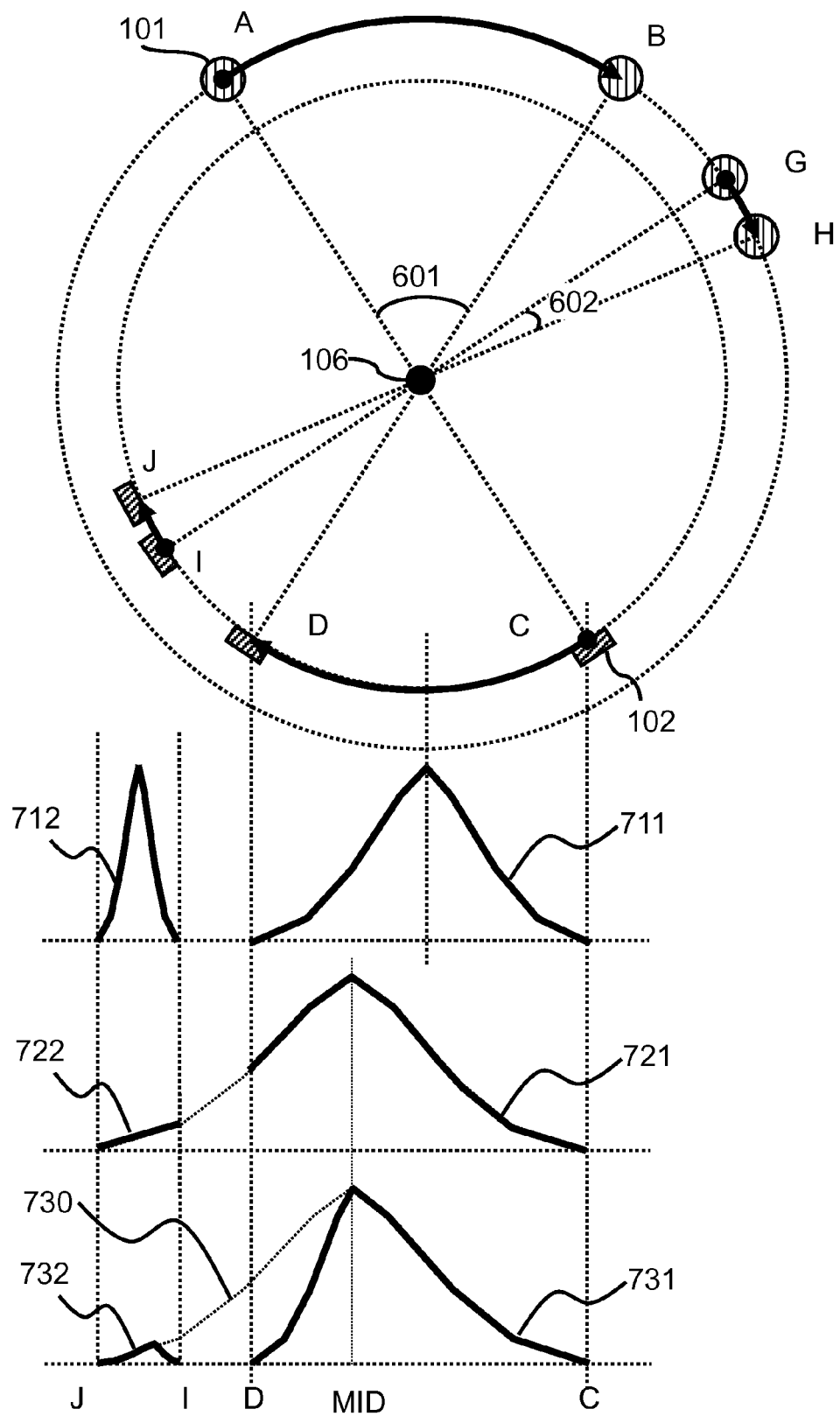
FIG. 13 illustrates the measurement range and the profile of the weight according to the fourth embodiment.

In the present embodiment, there are various weight variation profiles applied to the rotationally measured images obtained from the measured images that are acquired in the respective unit rotation angle ranges. FIG. 13 illustrates a specific example of the weight variation profiles according to the present embodiment. In this example here, similar to the third embodiment, the unit rotation angle range is defined as two ranges; the first unit rotation angle range 601 in which the X-ray source 101 moves rotationally from the position A to the position B, and the second unit rotation angle range 602 in which the X-ray source 101 moves rotationally from the position G to the position H. At this timing, the detector 102 moves rotationally from the position C to the position D, and from the position I to the position J in the respective ranges. The graphs 721 and 722 or the graphs 731 and 732 in FIG. 13 illustrate the weight variation profiles for the respective measurement angles of the present embodiment. For comparison, the weight variation profiles 711 and 712 are also shown here for the respective measurement angles of the third embodiment.

As illustrated in the figure, the weight variation profile 721 and 722 of the present embodiment has the shape taking a maximum value at the center of the angular direction in the entire unit rotation angle ranges for acquiring the measured images, and decreasing monotonously toward the edges. Specifically, the weight variation profile has the shape taking the maximum value at the center MID of the rotation angle range between the position C and the position J, and decreasing monotonously toward the edges (the position C and the position J). In other words, the intensity of the weight for the rotationally measured image is attenuated more, as the measurement angle of the rotationally measured image comes closer to the edge, within the rotation angle ranges of the measurement for obtaining one reconstructed image.

The weight variation profile may take the profile 731 and 732 as shown in the lowermost part of the figure. The weight variation profile 731 and 732 has the shape that only the maximum value of the weight applied to the rotationally measured images within each of the unit rotation angle ranges varies along the profile 730, where along the profile 730 taking the maximum value at the center of the angular direction in the entire unit rotation angle ranges and monotonously decreasing toward edges. Here, within each of the unit rotation angle ranges, the each profile 731 and 732 has the shape taking the maximum value at the center, and monotonously decreases toward the edges. In this situation, in the unit rotation angle ranges respectively on both edges, the profile from the edge to the center of the unit rotation angle range has the shape that follows the profile 730.

Specifically, the profile corresponds to the profile 731 taking the maximum value at the center MID in the angular range from the position C to the position J, and taking the minimum value at the position C and the position D, and the profile 732 taking the maximum value at the center between the position I and the position J, and taking the minimum value at the position I and the position J. The maximum value of the profile 732 is a value on the profile 730. In other words, the intensity of the weight for the rotationally measured image is attenuated more, as the measurement angle of the rotationally measured image comes closer to the edge of the unit rotation angle range. The maximum value in the unit rotation angle range becomes smaller, as the unit rotation angle range becomes distant from the center of the rotation angle range for obtaining the rotationally measured images of all the measurements.

In the present embodiment, the weight determiner 322 determines the weight to be applied to each of the rotationally measured images according to any of the aforementioned methods.

Figure 14:
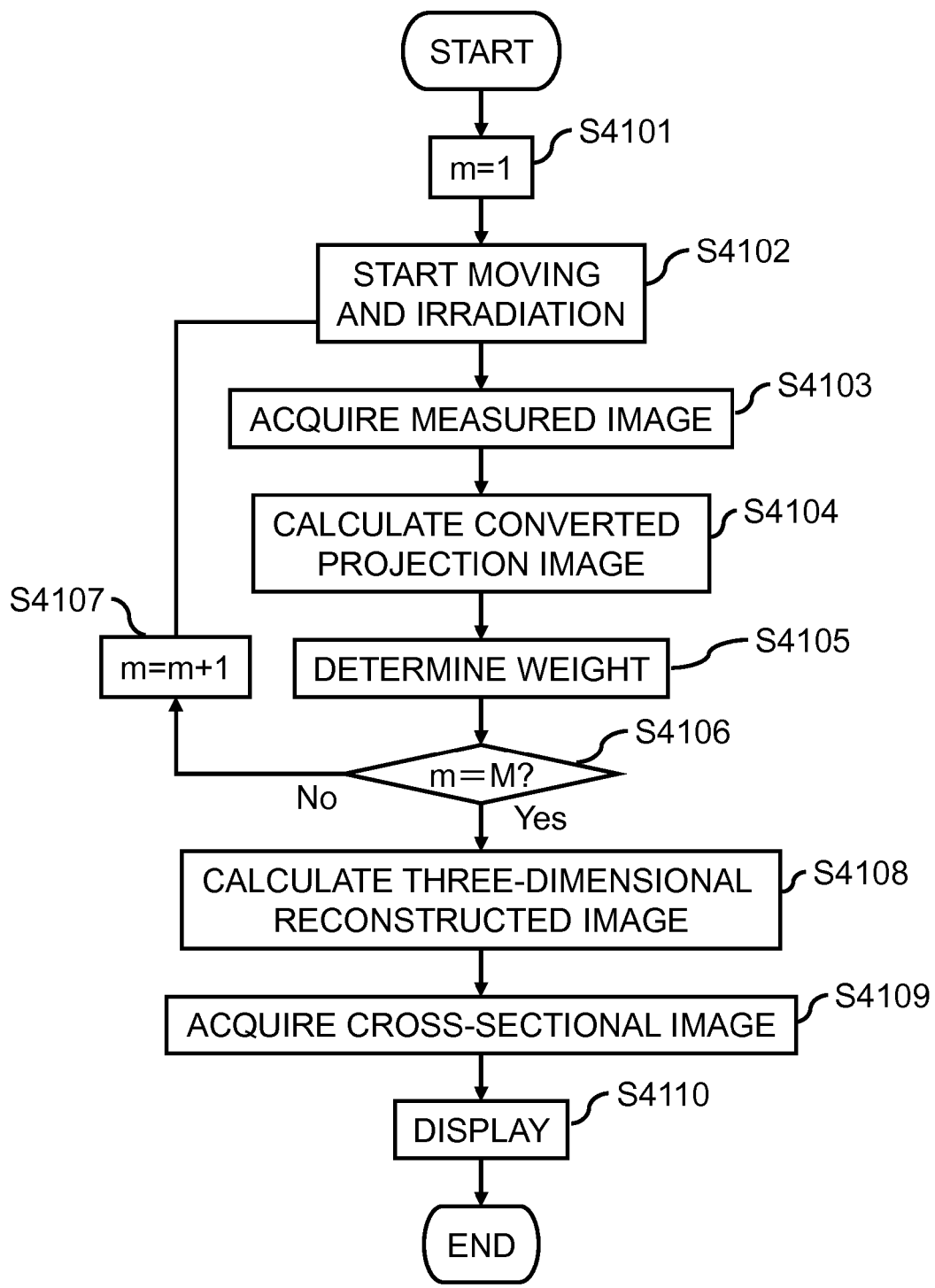
FIG. 14 is a flowchart showing the imaging process of the fourth embodiment.

Next, a flow of the imaging process by the controller 103 of the present embodiment will be explained. FIG. 14 is a flow of the imaging process according to the present embodiment. Here, the measuring processor 310 performs imaging of each of M regions (unit rotation angle ranges), having the rotation angle range less than 180 degrees. It is assumed that m is a counter. The weight for each measurement angle in each of the regions is determined in advance by the weight determiner 322.

The measuring processor 310 initializes the counter m (step S4101). The measuring processor 310 starts rotational movement of the X-ray source 101 and the detector 102, and radiation of X-rays (step S4102). Then, the measuring processor 310 acquires measured image in the m-th unit rotation angle range being defined in advance (step S4103). In receipt of the measured image, the converter 321 calculates the rotationally measured image and the measurement angle thereof (step S4104). Then, the weight determiner 322 determines the weight to be applied to each of the rotationally measured images (step S4105).

The measuring processor 310 repeats the processing of the step S4103 and step S4105, until reaching the M-th unit rotation angle range (steps S4106 and S4107).

After the measurement of all the unit rotation angle ranges is completed, the reconstructor 323 applies the weights decided by the weight determiner 322 respectively to the rotationally measured images in all the unit rotation angle ranges, and a three-dimensional reconstructed image is obtained (step S4108). The display image generator 324 obtains a cross-sectional image of a predetermined plane from thus obtained three-dimensional reconstructed image (step S4109), and displays the cross-sectional image on the monitor (step S4110).

Also in the present embodiment, as the weight provided to the rotationally measured image upon reconstruction, at least one of the following may be used; the weight value, the smoothing region size, and the reconstruction filter.

In the present embodiment, after obtaining all the measured images within the entire unit rotation angle ranges, rotationally measured images of all the measured images are obtained, and then reconstruction processing is performed, but the order of processing is not limited to this example. By way of example, every time the measured image at each measurement angle is obtained, the rotationally measured image is obtained, and this process repeated for all the measured images. Then, after obtaining all the rotationally measured images for the entire unit rotation angle ranges, the reconstruction process may be performed.

It is further possible to configure such that every time the measured image at each measurement angle is obtained, the rotationally measured image is obtained, the weight is determined, and the weighted summation process of the reconstruction process is performed, taking the measurement angle into account. With this configuration, the memory for holding all the measured images and all the rotationally measured images is not necessary any more, thereby simplifying the configuration.

Also in the present embodiment, the X-ray imaging apparatus 120 is only required to acquire the measured image that the converter 321 is able to convert into the rotationally measured image being acquired by an apparatus in which the X-ray source 101 and the detector 102 rotationally move along the concentric circular paths about the rotation axis 106, and any layout, operations, and moving ranges of the X-ray source 101 and the detector 102 are applicable.

Also in the present embodiment, similar to the third embodiment, it may be configured such that a biological monitor, or the like, is provided, and the measuring processor 310 determines each unit rotation angle range for acquiring the measured image and a timing for acquiring the measured image.

Also in the present embodiment, the number of the unit rotation angle ranges for obtaining the measured images is not limited to two. For the case where the imaging is performed repeatedly and plural measured images are obtained at the same rotation angle on the circular path, the weight applied to the rotationally measured images obtained from the respective measured images, is assumed as a value obtained by dividing the weight determined by the weight determiner 322, by the number of the measured images overlapping one another.

As described so far, the X-ray imaging apparatus according to the present embodiment is provided with, the X-ray source 101 configured to irradiate the subject 104 with X-rays, the detector 102 configured to detect the X-rays, the measuring processor 310 configured to relatively move the X-ray source 101 and the detector 102 to acquire a measured image, and the image processor 320 configured to apply an arithmetic operation to the measured image so as to obtain an image, wherein the image processor 320 is provided with the converter 321 configured to convert the measured image, into a rotationally measured image acquired in a predetermined rotation angle range when the X-ray source 101 and the detector 102 rotationally move along the concentric circular paths, and the reconstructor 323 configured to apply a weight to the rotationally measured image, responsive to the measurement angle of the rotationally measured image, perform a reconstruction operation, and obtain a reconstructed image, and the predetermined rotation angle range for acquiring the rotationally measured image, includes at least one unit rotation angle range for sequentially acquiring the rotationally measured images, the unit rotation angle range is less than 180 degrees, and the weight provides the reconstructed image obtained from the rotationally measured images with intensity variation being equivalent to that of the reconstructed image obtained by the measurement when the rotation angle range is 180 degrees.

The weight may be determined so that the intensity of the weight for the rotationally measured image is attenuated more, as the measurement angle of the rotationally measured image comes closer to the edge of the rotation angle range of the measurement for obtaining one reconstructed image. In addition, the weight may be determined so that the intensity of the weight for the rotationally measured image is attenuated more, as the measurement angle of the rotationally measured image comes closer to the edge of the unit rotation angle range that is the rotation angle range for sequentially obtaining the rotationally measured images. Alternatively, the weight may be determined so that the maximum value in each of the unit rotation angle ranges for sequentially obtaining the rotationally measured images becomes smaller, as the unit rotation angle range is more distant from the center of the rotation angle range for obtaining the rotationally measured images of all the measurements.

The reconstructor 323 may obtain one reconstructed image from the rotationally measured images obtained in the plural unit rotation angle ranges. The image processor 320 is further provided with the weight determiner 322 to determine the weight, and the weight determiner 322 may use a predetermined evaluation value to optimize the weight. The weight may be at least one of the weight value by which the rotationally measured image at each measurement angle is multiplied, the region size for smoothing the rotationally measured image at each measurement angle, and the maximum frequency to be allowed to pass through the reconstruction filter applied to the rotationally measured image at each measurement angle.

The X-ray source 101 and the detector 102 may move in the direction along the bed 105 on which the subject 104 is placed, synchronously and in the directions opposite to each other, and the converter 321 may convert the measured image into the rotationally measured image, according to arithmetic operations including a geometric conversion process. The X-ray source 101 and the detector 102 may rotationally move relatively along the concentric circular paths, and the converter 321 may assume the measured image as the rotationally measured image. The reconstruction operation may be any of the back projection method and the filtered back-projection method. The image processor 320 may further be provided with the display image generator 324 configured to cut out a tomographic image of an arbitrary plane from the reconstructed image, and generate a display image. The arbitrary plane may be a plane parallel to the surface along the bed on which the subject is placed.

Furthermore, the image processing method of the present embodiment performs imaging with moving the X-ray source 101 and the detector 102 relatively, the X-ray source 101 configured to irradiate the subject 104 with X-rays and the detector 102 configured to detect the X-rays, and obtains a reconstructed image from the measured image being acquired, and the method converts the measured image into the rotationally measured image acquired in a predetermined rotation angle range when the X-ray source 101 and the detector 102 rotationally move along the concentric circular paths, provides the rotationally measured image with a weight that gives to the reconstructed image obtained from the rotationally measured images, intensity variation equivalent to that of the reconstructed image obtained by the measurement when the rotation angle range is 180 degrees, performs the reconstruction operation, obtains the reconstructed image, and assumes the unit rotation angle range is less than 180 degrees, being the rotation angle range for sequentially obtaining the rotationally measured images.

Therefore, according to the present embodiment, similar to the first embodiment, a cross-sectional image of the same quality may be obtained, by using the reconstruction method in the same manner as a CT scanner generally used, irrespective of the layout, operations, and moving range of the X-ray source and the detector.

Similar to the third embodiment, since the unit rotation angle range is defined in sync with a body motion, an image with low artifact may be obtained, even when a portion with large body motion is targeted for imaging. It is alternatively possible to present the variation in association with the body motion.

According to the present embodiment, one image is reconstructed from the measured images being separated in plural parts. Therefore, even though the imaging target portion is large in body motion, it is possible to obtain an image that is reconstructed by using only the projection data at the timing of displacement being equivalent to a level of the displacement caused by the body motion. With this configuration, the precision in values of the reconstructed image is improved, and an image quality of the tomographic image obtained from the reconstructed image is enhanced. In addition, since the number of the measured images used for the reconstruction process is increased, this enables noise reduction. The rotation angle range for reconstructing one image becomes wider, and thereby reducing the artifact. With the configuration above, an image quality of the reconstructed image is enhanced, and the image quality of the tomographic image being obtained is also enhanced.

Generally, the CT scanner that implements the rotation angle range of 180 degrees or more has to be large in scale. In addition, since the subject 104 is surrounded by the X-ray source 101 and the detector 102, it is difficult for the operator to be closer the subject 104 when the imaging is performed, and it is hard to handle the apparatus while conducting the medical operations, for instance. On the other hand, the X-ray imaging apparatus having the rotation angle range less than 180 degrees, or the X-ray imaging apparatus for tomosynthesis imaging with the X-ray source and the detector move along a linear path, is small in scale, and further this allows the operator to easily approach the subject 104 during the imaging. Therefore, according to each of the above embodiments, it is possible to obtain a cross-sectional image having an image quality equivalent to a conventional CT image, in any measuring site such as during medical operations.

In each of the above embodiments, it is configured such that the controller 103 being provided in the X-ray imaging apparatus implements the functions of the image processor 320, but this is not the only example. For example, the functions of the image processor 320 may be established on an information processing device being independent of the X-ray imaging apparatus, the information processing device being capable of sending and receiving data to and from the X-ray imaging apparatus.

Each of the above embodiments may be applied to various images, regarding the measurements of any portion, such as blood circulatory system, non-blood circulatory system, contrast, non-contrast, orthopedic, surgical, and dental, upon punctuation, upon radiotherapy treatment, and the like.

Each of the above embodiments may not be limited to the measurement using X-rays, but it is also effective for the measurement of light, X-rays, radiation, and the like.

EXPLANATION OF REFERENCES

100: X-ray tube, 101: X-ray source, 101': X-ray source, 102: detector, 102': detector, 103: controller, 104: subject, 105: bed, 106: rotation axis, 108: arm, 109: shifter, 110: X-ray imaging apparatus, 120: X-ray imaging apparatus, 130: X-ray imaging apparatus, 201: circular path, 202: circular path, 203: detection element, 204: X-ray source, 205: detection element, 310: measuring processor, 320: image processor, 321: converter, 322: weight determiner, 323: reconstructor, 324: display image generator, 401: reconstruction filter, 402: reconstruction filter, 403: reconstruction filter, 404: reconstruction filter, 500: variation profile, 501: intensity, 502: intensity, 503: intensity, 504: intensity, 505: intensity, 511: intensity, 512: intensity, 513: intensity, 514: intensity, 515: intensity, 521: intensity, 522: intensity, 523: intensity, 524: intensity, 525: intensity, 601: unit rotation angle range, 602: unit rotation angle range, 711: weight variation profile, 712: weight variation profile, 721: variation profile, 722: weight variation profile, 730: profile, 731: weight variation profile, 732: weight variation profile, 910: cross section, 920: cross section

What is claimed is:

1. A radiation imaging apparatus comprising,
an X-ray source configured to irradiate a subject with X-rays,
a detector configured to detect the X-rays,
a measuring processor configured to relatively move the X-ray source and the detector and obtain a measured image, and
an image processor configured to apply an arithmetic processing to the measured image to obtain an image, wherein,
the image processor comprises,
a converter to convert the measured image into a rotationally measured image acquired within a predetermined rotation angle range when the X-ray source and the detector move rotationally along concentric circular paths, and
a reconstructor configured to apply a weight responsive to a measurement angle, to the rotationally measured image, perform a reconstruction operation, and obtain a reconstructed image, wherein,
the predetermined rotation angle range for acquiring the rotationally measured image includes at least one unit rotation angle range for sequentially acquiring the rotationally measured images,
the unit rotation angle range is less than 180 degrees, and
the weight provides the reconstructed image obtained from the rotationally measured images, with intensity variation equivalent to the intensity variation of the reconstructed image obtained from a measurement using the rotation angle range of 180 degrees.

2. The radiation imaging apparatus according to claim 1, wherein,
the weight is determined so that intensity of the rotationally measured image is attenuated more, as the measurement angle of the rotationally measured image comes closer to an edge of the rotation angle range used for the measurement to obtain one reconstructed image.

3. The radiation imaging apparatus according to claim 1, wherein,
the weight is determined so that intensity of the rotationally measured image is attenuated more, as the measurement angle of the rotationally measured image comes closer to the edge of the unit rotation angle range.

4. The radiation imaging apparatus according to claim 3, wherein,
a maximum value of the weight in the unit rotation angle range becomes smaller, as the unit rotation angle range becomes distant from the center of the rotation angle range for obtaining the rotationally measured images of all the measurements.

5. The radiation imaging apparatus according to claim 2, wherein,
the measurement for obtaining one reconstructed image, in association with the rotation angle ranges being different from one another, is performed more than once.

6. The radiation imaging apparatus according to claim 3, wherein,
the reconstructor obtains one reconstruction image from rotationally measured images obtained in the unit rotation angle ranges more than one.

7. The radiation imaging apparatus according to claim 1, wherein,
the image processor further comprises a weight determiner configured to determine the weight, and the weight determiner uses a predetermined evaluation value to optimize the weight.

8. The radiation imaging apparatus according to claim 1, wherein,
the weight is at least one of the following; a weight value by which the rotationally measured image at each measurement angle is multiplied, a region size for smoothing the rotationally measured image at each measurement angle, and a maximum frequency allowed to pass through the reconstruction filter that is applied to the rotationally measured image at each measurement angle.

9. The radiation imaging apparatus according to claim 1, wherein,
the X-ray source and the detector move synchronously and in the directions opposite to each other, along a bed on which the subject is placed, and the converter converts the measured image into the rotationally measured image, according to arithmetic operations including a geometric transformation process.

10. The radiation imaging apparatus according to claim 1, wherein,
the X-ray source and the detector rotationally move relatively along the concentric circular paths, and the converter assumes the measured image as the rotationally measured image.

11. The radiation imaging apparatus according to claim 1, wherein,
the reconstruction operation is either of a back projection method and a filtered back-projection method.

12. The radiation imaging apparatus according to claim 1, wherein,
the image processor comprises a display image generator configured to cut out a tomographic image of an arbitrary plane from the reconstructed image, and generate a display image.

13. The radiation imaging apparatus according to claim 12, wherein,
the arbitrary plane is parallel to a surface along a bed on which the subject is placed.

14. An image processing method that performs imaging while moving an X-ray source and a detector relatively, the X-ray source being configured to irradiate a subject with X-rays and the detector being configured to detect the X-rays, and obtains a reconstructed image from a measured image being acquired,
the method converting the measured image into a rotationally measured image acquired when the X-ray source and the detector rotationally move along concentric circular paths,
providing the rotationally measured image with a weight that gives to the reconstructed image obtained from the rotationally measured images, intensity variation equivalent to that of the reconstructed image obtained by the measurement when the rotation angle range is 180 degrees,
performing a reconstruction operation, and obtaining the reconstructed image, wherein,
a predetermined rotation angle range for acquiring the rotationally measured image includes at least one unit rotation angle range for sequentially acquiring the rotationally measured images, and
the unit rotation angle is less than 180 degrees.

* * * * *